United States Patent [19]

Cliff

[11] 4,309,559
[45] Jan. 5, 1982

[54] SULPHONAMIDES USEFUL AS PESTICIDES

[75] Inventor: Geoffrey R. Cliff, Whittlesford, England

[73] Assignee: FBC Limited, Hauxton, England

[21] Appl. No.: 969,375

[22] Filed: Dec. 14, 1978

[30] Foreign Application Priority Data

Dec. 24, 1977 [GB] United Kingdom ............... 53902/77

[51] Int. Cl.³ .......................................... C07C 147/13
[52] U.S. Cl. ....................................... 560/12; 549/65;
560/13; 71/66; 560/151; 562/430; 71/67;
564/81; 564/96; 71/88; 564/97; 564/99; 71/90;
564/162; 424/336; 71/92; 424/337; 260/239 B;
71/94; 260/239.3 R; 260/326 S; 71/95;
260/326.5 SF; 260/340.9 R; 71/99; 260/343.5;
260/343.6; 71/100; 260/346.2 R; 260/347.2;
71/101; 260/454; 260/455 R; 71/103; 260/465
E; 260/502.6; 71/118; 544/60; 544/111;
424/244; 544/146; 544/147; 424/248.5;
544/359; 544/383; 424/273 P; 549/39; 549/59;
424/275; 424/277; 424/278; 424/279; 424/285;
424/302; 424/303; 424/304; 424/309; 424/319;
424/324; 424/327; 424/331; 546/192; 546/216;
548/378

[58] Field of Search ........................................ 560/12

[56] References Cited

U.S. PATENT DOCUMENTS

3,840,597 10/1974 Moore ................................ 260/556

FOREIGN PATENT DOCUMENTS

712762 7/1954 United Kingdom .
1486497 9/1977 United Kingdom .

OTHER PUBLICATIONS

Chem. Abstr., 51:14756, b,c,e,i, 14755 g,i, 49:1062 c,d, 48:11379f, 46:P472d–f.

*Primary Examiner*—Glennon H. Hollrah

*Attorney, Agent, or Firm*—Morgan, Finnegan, Pine, Foley & Lee

[57] ABSTRACT

Sulphonanilides of formula

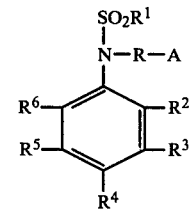

I and salts thereof, wherein $R^1$ represents alkyl or certain other groups;
R represents alkylene or alkenylene;
A represents —COOH, —COO alkyl, —CSSH, CN or certain related groups; or
R-A represents a group of formula

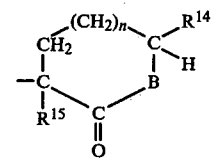

where $R^{14}$ represents hydrogen, alkyl or aryl, B represents oxygen or

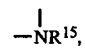

, $R^{15}$ represents hydrogen or alkyl, and n represents 0, 1 or 2; and
$R^2$-$R^6$ represent hydrogen; alkyl, halogen or certain other groups, are pesticides and plant growth regulants, especially herbicides and fungicides.

8 Claims, No Drawings

SULPHONAMIDES USEFUL AS PESTICIDES

This invention relates to new compounds and their production and to methods and compositions for combating pests and for regulating the growth of a plant.

Accordingly, the invention provides a method of combating pests at a locus infested or liable to be infested with them or of regulating the growth of a plant at a locus at which the plant is growing or is to grow, which method comprises applying to the locus a pest-combating or plant growth regulant amount of a compound which is a sulphonanilide of formula

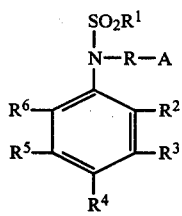

or salt thereof, wherein $R^1$ represents alkyl, substituted alkyl, cycloalkyl, aralkyl, substituted aralkyl, aryl, substituted aryl, a heterocyclic group, a substituted heterocyclic group, or a group of formula

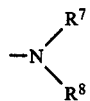

where $R^7$ and $R^8$ are the same or different and each represents a hydrogen atom, alkyl, substituted alkyl, aralkyl, substituted aralkyl, aryl or substituted aryl;
R represents alkylene or alkenylene;
A represents —COOH; —CSSH; —CEGR$^9$; —CENR$^{10}$R$^{11}$;

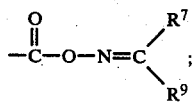

—CN; or —COR$^{12}$ or a carbonyl derivative or addition compound thereof; where E and G are the same or different and each represents an oxygen or sulphur atom; $R^9$ represents alkyl, substituted alkyl, aralkyl, substituted aralkyl, aryl or substituted aryl; $R^{10}$ and $R^{11}$ are the same or different and each represents a group as defined for $R^7$; or $R^{10}$ and $R^{11}$ together with the nitrogen atom to which they are attached form a heterocyclic group or a substituted heterocyclic group; or $R^{10}$ represents a hydrogen atom while $R^{11}$ represents a group of formula

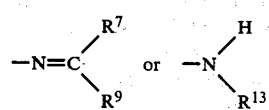

where $R^{13}$ represents a hydrogen atom or —COOR$^9$; and $R^{12}$ represents a hydrogen atom, alkyl, substituted alkyl, cycloalkyl, aralkyl, substituted aralkyl, aryl, substituted aryl, a heterocyclic group linked via a carbon atom in the group or such a heterocyclic group which is substituted; or
R-A represents a group of formula

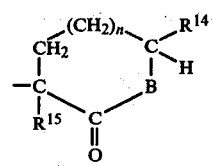

wherein $R^{14}$ represents a hydrogen atom, alkyl or aryl, B represents an oxygen atom or

$R^{15}$ represents a hydrogen atom or alkyl, and n represents 0, 1 or 2; and
$R^2$, $R^3$, $R^4$, $R^5$ and $R^6$ are the same or different and each represents a hydrogen atom; alkyl; substituted alkyl; hydroxy; alkoxy; —SCN; nitro; halogen; amino; substituted amino; mercapto; a group of formula —SR$^{16}$, —SOR$^{16}$, —SO$_2$R$^{16}$ or —OSO$_2$R$^{16}$ where $R^{16}$ represents alkyl, aryl or aralkyl; —SO$_2$NR$^7$R$^8$; or —COOR$^{12}$;
with the proviso that $R^2$, $R^3$, $R^4$, $R^5$ and $R^6$ do not each represent a hydrogen atom when R represents alkylene, $R^1$ represents phenyl or substituted phenyl, and A represents COOH or COOR$^9$ where $R^9$ represents alkyl.

The invention provides also a pesticidal or plant growth regulant composition containing the compound, especially such a composition comprising the compound together with at least one material selected from carriers, surface active agents, other pesticides, other plant growth regulants, antidotes and fertilizers.

Almost all the compounds are novel, and these the invention provides per se.

The invention provides the compound as defined above except that the proviso is replaced by the proviso that $R^2$, $R^3$, $R^4$ and $R^5$ do not each represent a hydrogen atom when $R^6$ represents a hydrogen atom, methoxycarbonyl or ethoxycarbonylmethyl, R represents alkylene, $R^1$ represents phenyl or substituted phenyl, and A represents benzoyl, COOH or COOR$^9$ represents alkyl.

The invention also provides a process for preparing the novel compounds, which process comprises:

(a) reacting a sulphonamide of formula:

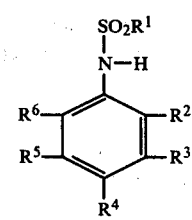

or salt thereof, with a halo derivative of formula X-R-A, wherein X represents a halogen atom and A, R, $R^1$, $R^2$, $R^3$, $R^4$, $R^5$ and $R^6$ are as defined above;

(b) acylating an arylamino derivative of formula

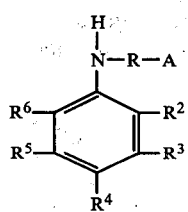

or salt thereof, with an acylating agent of formula $R^1SO_2Z$ or $(R^1SO_2)_2O$ where Z represents a halogen atom and A, R, $R^1$, $R^2$, $R^3$, $R^4$, $R^5$ and $R^6$ are as defined above;

(c) where A represents —COOH, hydrolysing a sulphonanilide of formula I or salt thereof in which A represents —COOR$^9$, —CONR$^{10}$R$^{11}$,

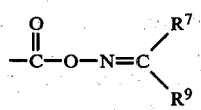

or —CN where $R^7$, $R^9$, $R^{10}$ and $R^{11}$ are as defined above;

(d) where A represents —COOR$^9$, esterifying a sulphonanilide of formula I or salt thereof in which A represents —COOH with an alcohol of formula $R^9OH$;

(e) where A represents —CEGR$^9$, reacting an acyl halide of formula

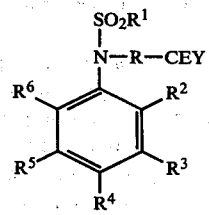

with an alcohol or mercaptan of formula $R^9GH$, where Y represents a halogen atom and E, G, R, $R^1$, $R^2$, $R^3$, $R^4$, $R^5$, $R^6$ and $R^9$ are as defined above;

(f) where A represents —CONR$^{10}$R$^{11}$, reacting the acyl halide of formula IV where E represents an oxygen atom with an amino derivative of formula HNR$^{10}$R$^{11}$, where R$^{10}$ and R$^{11}$ are as defined above;

(g) where A represents

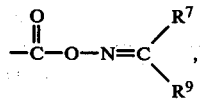

reacting the acyl halide of formula IV where E represents an oxygen atom with a hydroxylamine derivative of formula

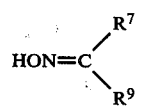

where $R^7$ and $R^9$ are as defined above;

(h) where A represents —COR$^{12}$ or a carbonyl derivative or addition compound thereof, decarboxylating a carboxylic acid of formula

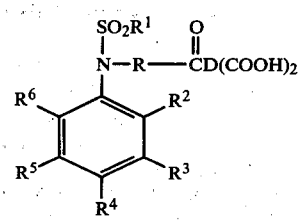

where DH$_2$ represents R$^{12}$, (i) where A represents a carbonyl derivative of —COR$^{12}$, reacting the corresponding compound in which A represents —COR$^{12}$ with a material of formula HMH to eliminate a molecule of water between them;

(j) where A represents

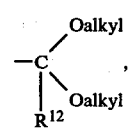

reacting the corresponding compound in which A represents —COR$^{12}$ with an orthoformate of formula CH(Oalkyl)$_3$;

(k) where A represents an oxime carbamate of

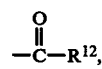

reacting the corresponding oxime with an isocyanate, or a carbamyl chloride, or with phosgene and then an amine;

(l) where A represents an addition compound of

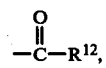

reacting the corresponding compound in which A represents —COR$^{12}$ with the compound with which it is required to make up the addition compound;

(m) to produce a salt of the sulphonanilide, salifying the sulphonanilide; or (n) to produce the sulphonanilide, desalifying a salt of the sulphonanilide.

Some of the intermediates in the production of the present compounds are novel, and the invention provides these per se.

The invention provides:
2',6'-dimethyl-1-propanesulphonanilide,
2',6'-dichloro-methanesulphonanilide,
2'-chloro-6'-methyl-methanesulphonanilide,
2',6'-dimethyl-1-butanesulphonanilide,
2',6'-dimethyl-ethanesulphonanilide,
2'-ethyl-methanesulphonanilide,
3',4'-dichloro-2-thiophenesulphonanilide,
3'-chloro-4'-fluoro-methanesulphonanilide,
3'-chloro-4'-methyl-methanesulphonanilide,
2'-methanesulphonyloxy-methanesulphonanilide,
2',6'-diisopropyl-methanesulphonanilide,
2'-methanesulphonyloxy-5'-nitro-methanesulphonanilide,
2',6'-dimethyl-dimethylaminosulphonanilide,
2'-chloro-6'-methyl-dimethylaminosulphonanilide,
2',3'-dichloro-methanesulphonanilide, 3',4'-dimethyl-methanesulphonanilide,
2',6'-dimethyl-2-propanesulphonanilide,
3',4'-dichloro-ethoxycarbonylmethanesulphonanilide,
3',5'-dichloro-methanesulphonanilide,
2',6'-dimethyl-4-morpholinesulphonanilide,
3',4'-dichloro-4-morpholinesulphonanilide,
or a salt of any of these.

The invention also provides a process for preparing the novel intermediates which are sulphonamides of formula II or salts thereof, which process comprises acylating an aniline of formula

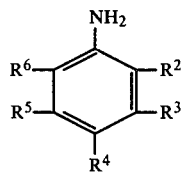

or salt thereof with an acylating agent of formula $R^1SO_2Z$ or $(R^1SO_2)_2O$.

The sulphonanilide of formula I may form salts. When $R^2$, $R^3$, $R^4$, $R^5$ or $R^6$ represents —COOH, or A represents —COOH or —CSSH, a salt may be formed with a base, e.g. sodium hydroxide. Such salts include metal, particularly alkali metal, especially sodium or potassium, salts and amine salts, e.g. methylamine or ethanolamine salts. The salts may be formed from the non-salt form (i.e. the non-salt form may be salified) in ways conventional for other salts, and may be converted to the non-salt form (i.e. desalified) in ways conventional for other salts. Thus, a salt may be formed by reaction of the non-salt form with a base, e.g. sodium hydroxide, and a salt with a base may be converted to the non-salt form by reaction with an acid, e.g. hydrochloric acid.

The sulphonamides of formula II may form salts. Salts may be formed from the non-salt form in ways conventional for other salts, and may be converted to the non-salt form in ways conventional for other salts. Thus salts may be formed by reaction of the non-salt form with a strong base, and may be converted to the non-salt form by reaction with an acid, e.g. hydrochloric acid. Salts include for example potassium salts.

When $R^{12}$ in

represents a hydrogen atom, the present sulphonanilides are aldehydes; when $R^{12}$ in

represents other than a hydrogen atom, the present sulphonanilides are ketones. In both cases, carbonyl derivatives are formed. The derivatives can be considered as being derived from the carbonyl group of A by reaction with elimination of a molecule of water. The derivatives include:
ketals, where A represents e.g.

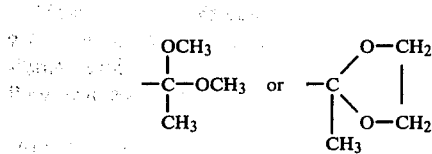

thioketals, where A represents e.g.

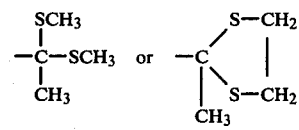

oximes, where A represents e.g.

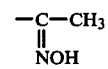

oxime esters, where A represents e.g.

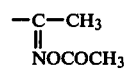

oxime ethers, where A represents e.g.

oxime carbamates, where A represents e.g.

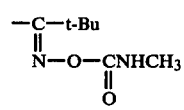

hydrazones, where A represents e.g.

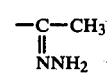

substituted hydrazones, for instance methylhydrazones, where A represents e.g.

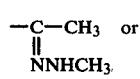

phenylhydrazones, where A represents e.g.

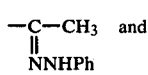

semicarbazones, where A represents e.g.

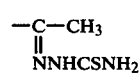

Carbonyl derivatives are well known in themselves.

The addition compounds include those with cyanide ion, bisulphite ion or ammonia. The ions may be for instance ammonium, sodium or potassium ions. Addition compounds of aldehydes and ketones are well known in themselves.

The present compounds are preferably prepared by reacting the sulphonamide of formula II or salt thereof with the halo derivative of formula X-R-A. X represents a halogen (ie. fluorine, chlorine, bromine or iodine) atom, preferably a chlorine or bromine atom. The reaction is usually conducted in the presence of an acid acceptor, e.g. potassium carbonate.

The present compounds may be prepared by acylating the arylamino derivative of formula III or salt thereof with an acylating agent of formula $(R^1SO_2)_2O$ or preferably $R^1SO_2Z$. Z usually represents a chlorine atom.

The present compounds in which A represents —COOH may be prepared by hydrolysing the compound in which A represents —COOR$^9$,

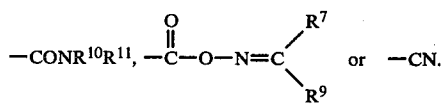

The hydrolysis is usually conducted in the presence of acid (e.g. sulphuric acid) or base (e.g. sodium hydroxide).

The present compounds in which A represents —COOR$^9$ may be prepared by esterifying the compound in which A represents —COOH. The esterification is usually conducted in the presence of acid (e.g. sulphuric acid).

The present compounds in which A represents —CEGR$^9$ may be prepared by acylating the alcohol or mercaptan of formula R$^9$GH with the acyl halide of formula IV. Y in formula IV represents a halogen, usually a chlorine, atom.

The present compounds in which A represents —CONR$^{10}$R$^{11}$ may be prepared by acylating the amino derivative of formula HNR$^{10}$R$^{11}$ with the acyl halide of formula IV where E represents an oxygen atom. Again Y usually represents a chlorine atom.

The compounds in which A represents —COR$^{12}$ may be prepared by decarboxylating a carboxylic acid of formula V. Decarboxylation may be brought about for example by heating. The carboxylic acid is preferably prepared in situ, for example by hydrolysis of its ester e.g. it ethyl ester.

The compounds in which A represents a carbonyl derivative of —COR$^{12}$ may be prepared by reacting the corresponding compound in which A represents —COR$^{12}$ with a material of formula HMH to eliminate a molecule of water between them. For instance, a compound in which A represents —COCH$_3$ may be reacted with ethylene glycol in the presence of acid to form the corresponding compound in which A represents

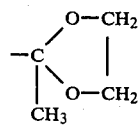

The compounds in which A represents

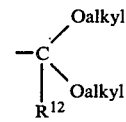

may be prepared by reacting the corresponding compound in which A represents —COR$^{12}$ with an orthoformate of formula CH(Oalkyl)$_3$, usually in the presence of for example an acid such as 4-toluenesulphonic acid or hydrogen chloride, or ammonium chloride or ferric chloride.

The sulphonamide of formula II or salt thereof may be prepared by acylating an aniline of formula VI or salt thereof with the acylating agent of formula $(R^1SO_2)_2O$ or preferably $R^1SO_2Z$. Again Z usually represents a chlorine atom.

The acyl halide of formula IV may be prepared by reacting a sulphonanilide of formula I in which A represents —COOH or —CSSH or salt thereof with thionyl halide, phosphoryl halide, phosphorus pentahalide or oxalyl halide, particularly the chlorides and especially thionyl chloride.

The present processes are usually conducted in the presence of a solvent, and usually are carried out at 0–200 e.g. 0°–150° C. The solvent may be for example water or an ether, ketone, hydrocarbon, amide or alcohol. The pressure may be for instance 0.5 to 10 atmospheres, conveniently ambient pressure.

Any substituted alkyl group in the present compounds preferably has as the substituent(s) one or more of halogen, alkoxy, furyl, phthalimido, —SCN, amino, substituted amino (e.g. amino mono- or di-substitited by alkyl or acyl), alkoxycarbonyl, carboxy,

benzoyloxy, alkanoyloxy, alkylsulphonyloxy, nitrile and hydroxy. In the case of R$^2$, R$^3$, R$^4$, R$^5$ and R$^6$, a preferred such substituted alkyl group is —CF$_3$.

Any acyl group is preferably alkanoyl.

Any substituted aryl group is preferably aryl substituted by one or more of halogen, alkyl, alkoxy, alkylsulphonyloxy, nitro, —SCN and trifluoromethyl.

Any substituted aralkyl group is preferably substituted on the aryl nucleus. The substituent(s) are preferably selected from halogen, alkyl, alkoxy, nitro, —SCN, alkylsulphonyloxy and trifluoromethyl.

When any of the present symbols represents a substituted or unsubstituted group, it is preferably unsubstituted. When it is substituted by more than one substituent, the substituents are usually the same, e.g. all chlorine or all methyl.

Any alkyl group involved in the present symbols is preferably of 1–15, e.g. 1–8, especially 1–6, carbon atoms, for example methyl, ethyl, propyl, isopropyl, butyl or hexyl. Any cycloalkyl group is preferably of 3–7 carbon atoms, especially cyclohexyl or cyclopentyl. Any aryl group is preferably phenyl. Any aralkyl group is preferably phenylalkyl, e.g. of 7–10 carbon atoms, especially benzyl. Any halogen is preferably fluorine, chlorine or bromine especially chlorine. Any alkoxy is preferably of 1–6 carbon atoms, e.g. methoxy. Any alkanoyl group is preferably of 2–7 carbon atoms. The alkylene or alkenylene group which R represents may be branched or straight chain. Usually it contains 1–6, preferably 1–3, carbon atoms. Especially preferred when A represents —COR$^{12}$ or a carbonyl derivative or addition compound thereof is R representing methylene; when A represents other values, it is especially preferred that R represents

where R$^{18}$ represents alkyl of 1–5, preferably 1 or 2, carbon atoms.

The heterocyclic or substituted heterocyclic group which R$^1$ may represent may be linked via a ring carbon or ring hetero atom. Any heterocyclic group involved in the present symbols is usually a single hetero ring containing 3 to 7 ring atoms of which 1–3, e.g. 1 or 2, are hetero atoms, each hetero atom being nitrogen, sulphur or oxygen, to which hetero ring a benzene ring is optionally fused. The heterocyclic group may be for example furyl, thienyl, piperidyl, pyrrolyl, piperazinyl, morpholinyl or benzofuranyl. Any substituent on a heterocyclic group may be for instance alkyl e.g. methyl, oxo, nitro, or halogen e.g. chlorine.

Preferably, the heterocyclic group which —NR$^{10}$R$^{11}$ may represent is a single hetero ring containing 5–7, e.g. 5 or 6, ring atoms of which besides the nitrogen atom there may be 1 or 2 further hetero atoms, each hetero atom being oxygen, sulphur or nitrogen, to which hetero ring a benzene ring is optionally fused. The heterocyclic group is preferably piperazino, pyrrolidino, piperidino or morpholino. Any substituent may be for instance alkyl, e.g. methyl, oxo, nitro, or halogen, e.g. chlorine.

Thus, in a preferred embodiment,

R$^1$ represents alkyl of 1–15 carbon atoms; alkyl of 1–15 carbon atoms substituted by one or more of halogen, alkoxy of 1–6 carbon atoms, alkoxycarbonyl of 2–7 carbon atoms, carboxy,

phthalimido, —SCN, benzoyloxy, alkanoyloxy of 2–7 carbon atoms, alkylsulphonyloxy of 1–6 carbon atoms, furyl, nitrile, hydroxy, amino and amino mono- or di-substituted by groups selected from alkyl of 1–15 carbon atoms and alkanoyl of 2–7 carbon atoms; cycloalkyl of 3–7 carbon atoms; phenylalkyl of 7–10 carbon atoms; phenylalkyl of 7–10 carbon atoms substituted on the phenyl nucleus by one or more of halogen, alkyl of 1–6 carbon atoms, alkoxy of 1–6 carbon, nitro, —SCN, alkylsulphonyloxy of 1–6 carbon atoms and trifluoromethyl; phenyl; phenyl substituted by one or more of halogen, alkyl of 1–6 carbon atoms, alkoxy of 1–6 carbon atoms, alkylsulphonyloxy of 1–6 carbon atoms, nitro, —SCN and trifluoromethyl; a heterocyclic group which is a single hetero ring containing 3 to 7 ring atoms of which 1–3 are hetero atoms, each hetero atom being nitrogen, sulphur or oxygen, to which hetero ring a benzene ring is optionally fused; such a heterocyclic group substituted by one or more of alkyl of 1–6 carbon atoms, oxo, nitro and halogen; or a group of formula

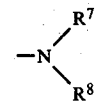

where R$^7$ and R$^8$ are the same or different and each represents a hydrogen atom; alkyl of 1–15 carbon atoms; alkyl of 1–15 carbon atoms substituted by one or more of halogen, alkoxy of 1–6 carbon atoms, alkoxycarbonyl of 2–7 carbon atoms, carboxy,

phthalimido, —SCN, benzoyloxy, alkanoyloxy of 2–7 carbon atoms, alkylsulphonyloxy of 1–6 carbon atoms, furyl, nitrile, hydroxy, amino and amino mono- or di-substituted by groups selected from alkyl of 1–15 carbon atoms and alkanoyl of 2–7 carbon atoms; phenylalkyl of 7–10 carbon atoms; phenylalkyl of 7–10 carbon atoms substituted on the phenyl nucleus by one or more of halogen, alkyl of 1–6 carbon atoms, alkoxy of 1–6 carbon atoms, nitro, —SCN, alkylsulphonyloxy of 1–6 carbon atoms and trifluoromethyl; phenyl; or phenyl substituted by one or more of halogen, alkyl of 1–6 carbon atoms, alkoxy of 1–6 carbon atoms, alkylsulphonyloxy of 1–6 carbon atoms, nitro, —SCN and trifluoromethyl;

R represents alkylene or alkenylene of 1–6 carbon atoms;

A represents —COOH; —CSSH; —CEGR$^9$; —CENR$^{10}$R$^{11}$;

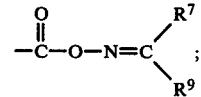

—CN; or —COR$^{12}$ or a carbonyl derivative or addition compound thereof; where E and G are the same or different and each represents an oxygen or sulphur atom, R$^9$ represents alkyl of 1–15 carbon atoms; alkyl of 1–15 carbon atoms substituted by one or more of halogen, alkoxy of 1–6 carbon atoms, alkoxycarbonyl of 2–7 carbon atoms, carboxy,

phthalimido, —SCN, benzoyloxy, alkanoyloxy of 2–7 carbon atoms, alkylsulphonyloxy of 1–6 carbon atoms, furyl, nitrile, hydroxy, amino and amino mono- or di-substituted by groups selected from alkyl of 1–15 carbon atoms and alkanoyl of 2–7 carbon atoms; phenylalkyl of 7–10 carbon atoms; phenylalkyl of 7–10 carbon atoms substituted on the phenyl nucleus by one or more of halogen, alkyl of 1–6 carbon atoms, alkoxy of 1–6 carbon atoms, nitro, —SCN, alkylsulphonyloxy of 1–6 carbon atoms and trifluoromethyl; phenyl; or phenyl substituted by one or more of halogen, alkyl of 1–6 carbon atoms, alkoxy of 1–6 carbon atoms, alkylsulphonyloxy of 1–6 carbon atoms, nitro, —SCN and trifluoromethyl; R$^{10}$ and R$^{11}$ are the same or different and each represents a group as defined for R$^7$ immediately above; or R$^{10}$ and R$^{11}$ together with the nitrogen atom to which they are attached form a heterocyclic group which is a single hetero ring containing 5-7 ring atoms of which besides the nitrogen atom there may be 1 or 2 further hetero atoms, each hetero atom being oxygen, sulphur or nitrogen, to which hetero ring a benzene ring is optionally fused; such a heterocyclic group substituted by one or more of alkyl of 1-6 carbon atoms, oxo, nitro and halogen; or $R^{10}$ represents a hydrogen atom while $R^{11}$ represents a group of formula

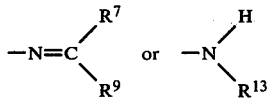

where $R^{13}$ represents a hydrogen atom or —COOR$^9$; and $R^{12}$ represents a hydrogen atom, alkyl of 1-15 carbon atoms; alkyl of 1-15 carbon atoms substituted by one or more of halogen, alkoxy of 1-6 carbon atoms, alkoxycarbonyl of 2-7 carbon atoms, carboxy,

phthalimido, —SCN, benzoyloxy, alkanoyloxy of 2-7 carbon atoms, alkylsulphonyloxy of 1-6 carbon atoms, furyl, nitrile, hydroxy, amino and amino mono- or di-substituted by groups selected from alkyl of 1-15 carbon atoms and alkanoyl of 2-7 carbon atoms; cycloalkyl of 3-7 carbon atoms; phenylalkyl of 7-10 carbon atoms; phenylalkyl of 7-10 carbon atoms substituted on the phenyl nucleus by one or more of halogen, alkyl of 1-6 carbon atoms, alkoxy of 1-6 carbon atoms, nitro, —SCN, alkylsulphonyloxy of 1-6 carbon atoms and trifluoromethyl; phenyl; phenyl substituted by one or more of halogen, alkyl of 1-6 carbon atoms, alkoxy of 1-6 carbon atoms, alkylsulphonyloxy of 1-6 carbon atoms, nitro, —SCN and trifluoromethyl; a heterocyclic group linked via a carbon atom in the group, which group is a single hetero ring containing 3 to 7 ring atoms of which 1-3 are hetero atoms, each hetero atom being nitrogen, sulphur or oxygen, to which hetero ring a benzene ring is optionally fused; or such a heterocyclic group substituted by one or more of alkyl of 1-6 carbon atoms, oxo, nitro and halogen; or R-A represents a group of formula

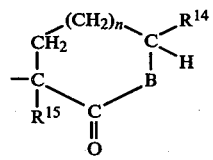

wherein $R^{14}$ represents a hydrogen atom, alkyl of 1-6 carbon atoms or phenyl, B represents an oxygen atom or

$R^{15}$ represents a hydrogen atom or alkyl of 1-6 carbon atoms, and n represents 0, 1 or 2;

$R^2$, $R^3$, $R^4$, $R^5$ and $R^6$ are the same or different and each represents a hydrogen atom; alkyl of 1-15 carbon atoms; alkyl of 1-15 carbon atoms substituted by one or more of halogen, alkoxy of 1-6 carbon atoms, alkoxycarbonyl of 2-7 carbon atoms, carboxy,

phthalimido, —SCN, benzoyloxy, alkanoyloxy of 2-7 carbon atoms, alkylsulphonyloxy of 1-6 carbon atoms, furyl, nitrile, hydroxy, amino and amino mono- or di-substituted by groups selected from alkyl of 1-15 carbon atoms and alkanoyl of 2-7 carbon atoms; hydroxy; alkoxy of 1-6 carbon atoms; —SCN; nitro; mercapto; a halogen atom; amino; amino mono- or di-substituted by groups selected from alkyl of 1-15 carbon atoms and alkanoyl of 2-7 carbon atoms; a group of formula —SR$^{16}$, —SOR$^{16}$, —SO$_2$R$^{16}$ or —OSO$_2$R$^{16}$ where R$^{16}$ represents alkyl of 1-6 carbon atoms, phenyl or phenylalkyl of 7-10 carbon atoms; —SO$_2$NR$^7$R$^8$ where R$^7$ and R$^8$ are as defined immediately above; or —COOR$^{12}$ where R$^{12}$ is as defined immediately above, with the proviso that R$^2$, R$^3$, R$^4$, R$^5$ and R$^6$ do not each represent a hydrogen atom when R represents alkylene of 1-6 carbon atoms, R$^1$ represents phenyl or phenyl substituted by one or more of halogen, alkyl of 1-6 carbon atoms, alkoxy of 1-6 carbon atoms, alkylsulphonyloxy of 1-6 carbon atoms, nitro, —SCN and trifluoromethyl, and A represents COOH or COOR$^9$ where R$^9$ represents alkyl of 1-15 carbon atoms. Within this embodiment, there are two preferred aspects. In one aspect, R$^1$ represents other than phenyl or substituted phenyl. In the other aspect, 3 or 4 of R$^2$, R$^3$, R$^4$, R$^5$ and R$^6$ each represent a hydrogen atom.

In a particular embodiment of the present compounds,

R$^1$ represents alkyl, substituted alkyl, cycloalkyl, aralkyl, substituted aralkyl, aryl, substituted aryl, or a group of formula

where R$^7$ and R$^8$ are the same or different and each represents a hydrogen atom, alkyl, substituted alkyl, aralkyl, substituted aralkyl, aryl or substituted aryl;

R represents alkylene;

A represents —COOH, —CSSH, —CEGR$^9$, —CENR$^{10}$R$^{11}$,

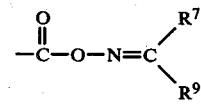

or —CN; where E and G are the same or different and each represents an oxygen or sulphur atom; R$^9$ represents alkyl, substituted alkyl, aralkyl, substituted aralkyl, aryl or substituted aryl; R$^{10}$ and R$^{11}$ are the same or different and each represents a group as defined for R$^7$; or R$^{10}$ and R$^{11}$ together with the nitrogen atom to which they are attached form a heterocyclic group; or R$^{10}$ represents a hydrogen atom while R$^{11}$ represents a group of formula

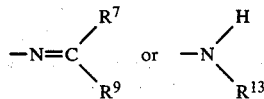

where $R^{13}$ represents a hydrogen atom or —$COOR^9$ (in which $R^9$ represents particularly ethyl); and $R^2$, $R^3$, $R^4$, $R^5$ and $R^6$ are the same or different and each represents a hydrogen atom, alkyl, substituted alkyl, alkoxy, —SCN, nitro, mercapto, alkylmercapto, amino or a halogen atom;

with the proviso that $R^2$, $R^3$, $R^4$, $R^5$ and $R^6$ do not each represent a hydrogen atom while both $R^1$ represents phenyl or substituted phenyl and A represents —COOH or $COOR^9$ where $R^9$ represents alkyl. Preferably, within this embodiment, $R^1$ represents alkyl of 1–15 carbon atoms; alkyl of 1–15 carbon atoms substituted by one or more of halogen, alkoxy of 1–6 carbon atoms, amino and amino mono- or di-substituted by groups selected from alkyl of 1–15 carbon atoms and alkanoyl of 2–7 carbon atoms; cycloalkyl of 3–7 carbon atoms; phenylalkyl of 7–10 carbon atoms; phenylalkyl of 7–10 carbon atoms substituted on the phenyl nucleus by one or more of halogen, alkyl of 1–6 carbon atoms, alkoxy of 1–6 carbon, nitro and trifluoromethyl; phenyl; or phenyl substituted by one or more of halogen, alkyl of 1–6 carbon atoms, alkoxy of 1–6 carbon atoms, nitro and trifluoromethyl; or a group of formula

where $R^7$ and $R^8$ are the same or different and each represents a hydrogen atom; alkyl of 1–15 carbon atoms; alkyl of 1–15 carbon atoms substituted by one or more of halogen, alkoxy of 1–6 carbon atoms, amino and amino mono- or di-substituted by groups selected from alkyl of 1–15 carbon atoms and alkanoyl of 2–7 carbon atoms; phenylalkyl of 7–10 carbon atoms; phenylalkyl of 7–10 carbon atoms substituted on the phenyl nucleus by one or more of halogen, alkyl of 1–6 carbon atoms, alkoxy of 1–6 carbon atoms, nitro and trifluoromethyl; phenyl; or phenyl substituted by one or more of halogen, alkyl of 1–6 carbon atoms, alkoxy of 1–6 carbon atoms, nitro and trifluoromethyl;

R represents alkylene of 1–6 carbon atoms;

A represents —COOH, —CSSH, —CEGR$^9$, —CENR$^{10}$R$^{11}$,

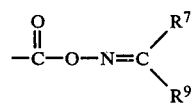

or —CN; where E and G are the same or different and each represents an oxygen or sulphur atom; $R^9$ represents alkyl of 1–15 carbon atoms; alkyl of 1–15 carbon atoms substituted by one or more of halogen, alkoxy of 1–6 carbon atoms, amino and amino mono- or di-substituted by groups selected from alkyl of 1–15 carbon atoms and alkanoyl of 2–7 carbon atoms; phenylalkyl of 7–10 carbon atoms; phenylalkyl of 7–10 carbon atoms substituted on the phenyl nucleus by one or more of halogen, alkyl of 1–6 carbon atoms, alkoxy of 1–6 carbon atoms, nitro and trifluoromethyl; phenyl; or phenyl substituted by one or more of halogen, alkyl of 1–6 carbon atoms, alkoxy of 1–6 carbon atoms, nitro and trifluoromethyl; $R^{10}$ and $R^{11}$ are the same or different and each represents a group as defined for $R^7$ immediately above; or $R^{10}$ and $R^{11}$ together with the nitrogen atom to which they are attached form a monocyclic heterocyclic group containing 5 to 6 ring atoms of which besides the nitrogen atom there may be a further hetero atom, which hetero atom is oxygen or nitrogen; or $R^{10}$ represents a hydrogen atom while $R^{11}$ represents a group of formula

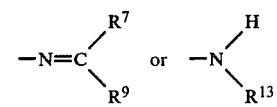

where $R^{13}$ represents a hydrogen atom or —$COOR^9$; and $R^2$, $R^3$, $R^4$, $R^5$ and $R^6$ are the same or different and each represents a hydrogen atom; alkyl of 1–15 carbon atoms; alkyl of 1–15 carbon atoms substituted by one or more halogen; alkoxy of 1–6 carbon atoms, amino and amino mono- or di-substituted by groups selected from alkyl of 1–15 carbon atoms and alkanoyl of 2–7 carbon atoms; alkoxy of 1–6 carbon atoms; —SCN; nitro; mercapto; alkylmercapto of 1–6 carbon atoms; amino or a halogen atom; with the proviso that $R^2$, $R^3$, $R^4$, $R^5$ and $R^6$ do not each represent a hydrogen atom while both $R^1$ represents phenyl or phenyl substituted by one or more of halogen, alkyl of 1–6 carbon atoms, alkoxy of 1–6 carbon atoms, nitro and trifluoromethyl, and A represents —COOH or $COOR^9$ where $R^9$ represents alkyl of 1–15 carbon atoms.

In another particular embodiment, $R^1$ represents alkyl, substituted alkyl, cycloalkyl, aralkyl, substituted aralkyl, aryl, substituted aryl, a heterocyclic group, a substituted heterocyclic group, or a group of formula

where $R^7$ and $R^8$ are the same or different and each represents a hydrogen atom, alkyl, substituted alkyl, aralkyl, substituted aralkyl, aryl or substituted aryl;

R represents alkylene or alkenylene;

A represents —COR$^{12}$ or a carbonyl derivative or addition compound thereof, where $R^{12}$ represents a hydrogen atom, alkyl, substituted alkyl, cycloalkyl, aralkyl, substituted aralkyl, aryl, substituted aryl, a heterocyclic group linked via a carbon atom in the group or such a heterocyclic group which is substituted; and $R^2$, $R^3$, $R^4$, $R^5$ and $R^6$ are the same or different and each represents a hydrogen atom; alkyl; substituted alkyl; alkoxy; —SCN; nitro; halogen; amino; substituted amino; mercapto; a group of formula —SR$^{16}$, —SOR$^{16}$ or —SO$_2$R$^{16}$ where R$^{16}$ represents alkyl, aryl or aralkyl; —SO$_2$NR$^7$R$^8$ where $R^7$ and $R^8$ are as defined immediately above; or —COOR$^{12}$ where $R^{12}$ is as defined immediately above. Within this embodiment, preferably, $R^1$ represents alkyl of 1–15 carbon atoms; alkyl of 1–15 carbon atoms substituted by one or more of halogen, alkoxy of 1-6 carbon atoms, amino and amino mono- or di-substituted by groups selected from alkyl of 1-15 carbon atoms and alkanoyl of 2-7 carbon atoms; cycloalkyl of 3-7 carbon atoms; phenylalkyl of 7-10 carbon atoms; phenylalkyl of 7-10 carbon atoms substituted on the phenyl nucleus by one or more of halogen, alkyl of 1-6 carbon atoms, alkoxy of 1-6 carbon, nitro and trifluoromethyl; phenyl; phenyl substituted by one or more of halogen, alkyl of 1-6 carbon atoms, alkoxy of 1-6 carbon atoms, alkylsulphonyloxy of 1-6 carbon atoms, nitro and trifluoromethyl; a heterocyclic group which is a single hetero ring containing 3 to 7 ring atoms of which 1 or 2 are hetero atoms, each hetero atom being nitrogen, sulphur or oxygen, to which hetero ring a benzene ring is optionally fused; such a heterocyclic group substituted by one or more of alkyl of 1-6 carbon atoms, nitro and halogen; or a group of formula

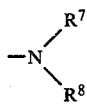

where $R^7$ and $R^8$ are the same or different and each represents a hydrogen atom; alkyl of 1-15 carbon atoms; alkyl of 1-15 carbon atoms substituted by one or more of halogen, alkoxy of 1-6 carbon atoms, amino and amino mono- or di-substituted by groups selected from alkyl of 1-15 carbon atoms and alkanoyl of 2-7 carbon atoms; phenylalkyl of 7-10 carbon atoms; phenylalkyl of 7-10 carbon atoms substituted on the phenyl nucleus by one or more of halogen, alkyl of 1-6 carbon atoms, alkoxy of 1-6 carbon atoms, nitro and trifluoromethyl; phenyl; or phenyl substituted by one or more of halogen, alkyl of 1-6 carbon atoms, alkoxy of 1-6 carbon atoms, alkylsulphonyloxy of 1-6 carbon atoms, nitro and trifluoromethyl;

R represents alkylene or alkenylene of 1-6 carbon atoms;

A represents —$COR^{12}$ or a carbonyl derivative or addition compound thereof, where $R^{12}$ represents a hydrogen atom, alkyl of 1-15 carbon atoms; alkyl of 1-15 carbon atoms substituted by one or more of halogen, alkoxy of 1-6 carbon atoms, amino and amino mono- or di-substituted by groups selected from alkyl of 1-15 carbon atoms and alkanoyl of 2-7 carbon atoms; cycloalkyl of 3-7 carbon atoms; phenylalkyl of 7-10 carbon atoms; phenylalkyl of 7-10 carbon atoms substituted on the phenyl nucleus by one or more of halogen, alkyl of 1-6 carbon atoms, alkoxy of 1-6 carbon atoms, nitro and trifluoromethyl; phenyl; phenyl substituted by one or more of halogen, alkyl of 1-6 carbon atoms, alkoxy of 1-6 carbon atoms, alkylsulphonyloxy of 1-6 carbon atoms, nitro and trifluoromethyl; a heterocyclic group linked via a carbon atom in the group, which group is a single hetero ring containing 3 to 7 ring atoms of which 1 or 2 are hetero atoms, each hetero atom being nitrogen, sulphur or oxygen, to which hetero ring a benzene ring is optionally fused; or such a heterocyclic group substituted by one or more of alkyl of 1-6 carbon atoms, nitro and halogen; and $R^2$, $R^3$, $R^4$, $R^5$ and $R^6$ are the same or different and each represents a hydrogen atom; alkyl of 1-15 carbon atoms; alkyl of 1-15 carbon atoms substituted by one or more of halogen, alkoxy of 1-6 carbon atoms, amino and amino mono- or di-substituted by groups selected from alkyl of 1-15 carbon atoms and alkanoyl of 2-7 carbon atoms; alkoxy of 1-6 carbon atoms; —SCN; nitro; mercapto; a halogen atom; amino; amino mono- or di-substituted by groups selected from alkyl of 1-15 carbon atoms and alkanoyl of 2-7 carbon atoms; a group of formula —$SR^{16}$, —$SOR^{16}$ or —$SO_2R^{16}$ where $R^{16}$ represents alkyl of 1-6 carbon atoms, phenyl or phenylalkyl of 7-10 carbon atoms; or —$COOR^{12}$ where $R^{12}$ is as defined immediately above.

Particularly preferred compounds are those wherein, $R^1$ represents alkyl of 1-4 carbon atoms, 2-phthalimidoethyl, ethoxycarbonylmethyl, nitrophenyl, morpholino, thienyl or dialkylamino of 2-8 carbon atoms;

R represents alkylene of 1-3 carbon atoms or alkenylene of 3 carbon atoms;

A represents —COOH; —$CENH_2$; —CN; —CONHPh; cycloalkyloxycarbonyl of 4-8 carbon atoms; morpholinocarbonyl; —$CONHNH_2$; —$CONHCH_2$ COOalkyl of 1-4 carbon atoms; —CONHNHCOO alkyl of 1-4 carbon atoms;

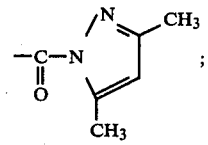

—$COOR^{17}$ or —$CON(R^{17})_2$ where $R^{17}$ represents alkyl of 1-5 carbon atoms; —$COCH_3$; —$COCH_2OH$;

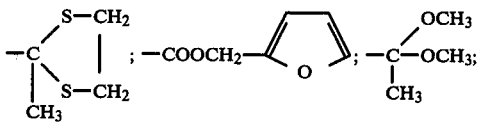

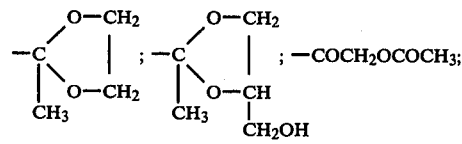

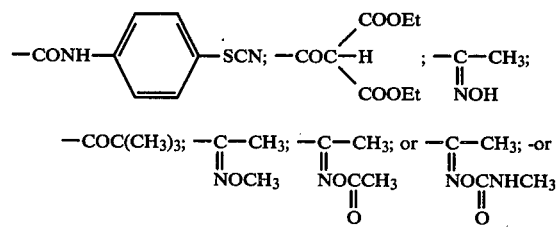

R-A represents

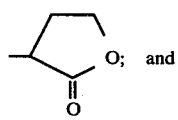

3 or 4 or $R^2$, $R^3$, $R^4$, $R^5$ and $R^6$ each represent a hydrogen atom and the remainder are the same or different and each represents alkyl of 1-3 carbon atoms, halogen, hydroxy, phenylmercapto, —SCN, nitro, alkoxy of 1-6 carbon atoms, trifluoromethyl, phenylsulphonyl, or methylsulphonyloxy.

In a particularly preferred group, 3 or 4 of $R^2$, $R^3$, $R^4$, $R^5$ and $R^6$ each represent a hydrogen atom. When A represents $-COR^{12}$ or a carbonyl derivative or addition compound thereof, it is particularly preferred that $R^3$, $R^4$ and $R^5$ or $R^2$, $R^3$, $R^5$ and $R^6$ each represent a hydrogen atom.

In a particularly preferred group,
$R^1$ represents alkyl of 1–4 carbon atoms or thienyl,
R represents methylene,
A represents $-COCH_3$,

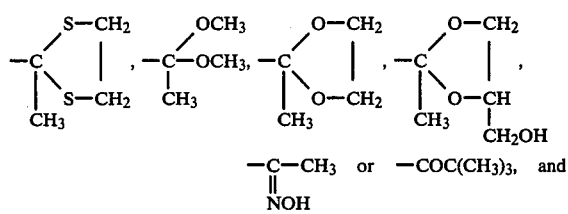

$$-\underset{\underset{NOH}{\|}}{C}-CH_3 \quad \text{or} \quad -COC(CH_3)_3, \text{ and}$$

3 or 4 of $R^2$, $R^3$, $R^4$, $R^5$ and $R^6$ each represent a hydrogen atom and the remainder are the same or different and each represents alkyl of 1–3 carbon atoms, halogen or alkoxy of 1–6 carbon atoms.

In another particularly preferred group,
$R^1$ represents alkyl of 1–4 carbon atoms;
R represents

in which $R^{18}$ represents methyl or ethyl;
A represents $-COOH$, $-COOR^{17}$, $-CENH_2$, $-CON(R^{17})_2$, $-CN$ or $-CONHPh$ where $R^{17}$ represents alkyl of 1–8 carbon atoms; and 3 or 4 of $R^2$, $R^3$, $R^4$, $R^5$ and $R^6$ each represent a hydrogen atom and the remainder are the same or different and each represents alkyl of 1–3 carbon atoms, halogen, alkoxy of 1–6 carbon atoms or trifluoromethyl.

Specific compounds are specified in the Examples.
Preferred specific compounds, particularly as herbicides, are
N-cyanomethyl-3',4'-dichloro-methanesulphonanilide
N-(1-[ethoxycarbonyl]ethyl)-2',6'-dimethyl-1-propanesulphonanilide; and
N-(1-[ethoxycarbonyl]ethyl)-2',6'-dimethyl-ethanesulphonanilide.

Another preferred specific compound, particularly as a fungicide, e.g. for use on vines or potatoes, is
N-(1-(methoxycarbonyl)ethyl)-2',6'-dimethyl-methanesulphonanilide.

Another preferred specific compound, particularly as a fungicide, is N-2-oxopropyl-2',6'-dimethyl-methanesulphonanilide.

The present compounds are pesticides and plant growth regulants. The compounds, especially those wherein A represents $-COOH$, $-CSSH$, $-CEGR^9$, $-CENR^{10}R^{11}$,

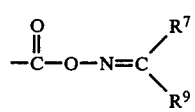

or $-CN$, are particularly active on plant physiology, affecting the growth of plants so that the compounds may be used as herbicides or plant growth regulants.

The present compounds, especially those wherein A represents $-COR^{12}$ or a carbonyl derivative or addition compound thereof, are also particularly useful as fungicides. The present compounds, especially those wherein A represents an oxime carbamate, are also particularly useful as insecticides. The present compounds are also anti-bacterial agents. The present compounds are outstandingly useful for combating fungus or weeds in crops.

The compounds may be employed to combat for instance chickweed (Stellaria media), fathen (Chenopodium album), wild oat (Avena fatua), blackgrass (Alopecurus myosuroides), barnyardgrass (Echinochloa cruss-galli) or crabgrass (Digitaria sanguinalis).

The compounds may be employed to combat weeds in for example food crops such as potatoes, vines, carrots or cereals, e.g. rice, wheat, barley or maize, ornamental crops, or plantation crops such as cotton.

For use as fungicides, the compounds are preferably employed to combat fungal diseases of plants, particularly of a crop specified above.

The compounds can be used to combat various fungal genera, e.g. Pythium, Phytophthora, Plasmopora, or Pyricularia.

The present compounds are normally employed in the form of compositions, which can be prepared by admixing the ingredients. Usually the compositions are initially produced in the form of concentrates, e.g. containing 0.5–85% of the present compound, and these are diluted with water or hydrocarbon, usually water, for application, generally such that the concentration of the compound is 0.05–5%, though in ultra low volume application the concentration may be higher, e.g. up to 20%. Percentages and parts in this specification are by weight unless otherwise indicated.

The compositions normally contain a surface active agent and/or a carrier.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present.

The carrier may be a liquid other than water, for example an organic solvent, such as a water immiscible solvent, e.g. a hydrocarbon which boils within the range 130°–270° C., in which the compound is dissolved or suspended. A concentrate containing a water immiscible solvent suitably also contains a surface-active agent so that the concentrate acts as a self-emulsifiable oil on admixture with water. The liquid may be a water-miscible solvent e.g. 2-methoxyethanol, methanol, propylene glycol, diethylene glycol, diethylene glycol monoethyl ether, formamide or methylformamide.

The carrier may be a solid, which may be finely divided. Examples of suitable solids are limestone, clays, sand, mica, chalk, attapulgite, diatomite, perlite, sepiolite, silicas, silicates, lignosulphonates, peat and solid fertilizers. The carrier can be of natural or synthetic origin or can be a modified natural material.

Wettable powders soluble or dispersable in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant e.g. a polyhalogenated alkane such as dichlorodifluoromethane, and suitably also with a solvent.

A flowable suspension concentrate may be formed if the compound has a low water solubility by grinding the compound with water, a wetting agent and a suspending agent.

A flowable suspension concentrate wherein the carrier is a hydrocarbon which boils within the range 130°–270° C. rather than water may be formed.

Thus the present composition can for example be solid (e.g. dust or granules) and contain a solid carrier, or liquid (e.g. an emulsifiable concentrate) and contain a liquid carrier which is a hydrocarbon which boils within the range 130°–270° C.

The term 'surface-active agent' is used in the broad sense to include materials variously called emulsifying agents, dispersing agents and wetting agents. Such agents are well known in the art.

The surface active agents used may comprise anionic surface active agents, for example soaps, mono- or diesters of phosphoric acid with fatty alcohol ethoxylates or salts of such esters, fatty alcohol sulphates such as sodium dodecyl sulphate, sodium octadecyl sulphate or sodium cetyl sulphate, ethoxylated fatty alcohol sulphates, ethoxylated alkylphenol sulphates, lignin sulphonates, petroleum sulphonates, alkyl-aryl sulphonates such as alkyl-benzene sulphonates or lower alkylnaphthalene sulphonates, e.g. butyl-naphthalene sulphonate, salts of sulphonated naphthalene-formaldehyde condensates, salts of sulphonated phenol-formaldehyde condensates, or more complex sulphonates such as the amide sulphonates e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products of fatty acid esters, fatty alcohols, fatty acid amides or fatty-, alkyl- or alkenyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, dialkyl sulphosuccinates, alkyl phenol ethoxylates, and fatty alkyl ethoxylates.

Non-ionic surface active agents are preferred.

The present active compound may be admixed with another pesticide, e.g. herbicide, fungicide, insecticide or anti-bacterial agent, or with another plant growth regulant. The invention provides a one pack presentation, in which the present compound is already mixed with other pesticide or plant growth regulant, and also a single package designed to hold the present compound and other pesticide or plant growth regulant in separate containers, for mixing, e.g. in a spray tank, for application. Particular advantages are obtained with mixtures with another herbicide or fungicide. The present compound may be used sequentially with another pesticide or plant growth regulant particularly with another herbicide or fungicide, e.g. one herbicide applied before planting or before emergence of a crop and the other herbicide applied after emergence of the crop.

The other herbicide may be for example one or more of a phenoxyaliphatic acid, substituted urea, triazine, phenol, nitrile, bipyridylium compound, substituted benzoic acid, halogenated aliphatic acid, carbamate, thiocarbamate, chloroacetamide, diazine or arsenic herbicide. In respect of selective herbicidal compositions for post-emergence use, the present compound may be used in admixture with for example a substituted phenoxyaliphatic acid; in respect of selective herbicidal compositions for pre-emergence use, the present compound may be used in admixture with for example a substituted urea or triazine; in respect of sequential selective herbicidal use, one may apply for example before emergence of the crop S-2,3-dichloroallyl di-isopropylthiocarbamate or S-2,3,3-trichloroallyl di-isopropylthiocarbamate and the present compound after emergence of the crop.

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity. Examples of the substituted phenoxyaliphatic acids which may be mentioned include 2,4-dichlorophenoxyacetic acid, 2-(2,4-dichlorophenoxy)propionic acid, 2-methyl-4-chlorophenoxyacetic acid, 2,4,5-trichlorophenoxyacetic acid, gamma-2,4-dichlorophenoxybutyric acid, gamma-2-methyl-4-chloro-phenoxybutyric acid, alpha-2-methyl-4-chlorophenoxypropionic acid, 2-(4-[2,4-dichlorophenoxy]phenoxy)propionic acid and 2-(4-[4-chlorophenoxy]phenoxy)propionic acid.

The substituted urea generally comprises a tri- or tetra-substituted urea such as N'-(3-chloro-4-methoxyphenyl)-N,N-dimethylurea, N'-(3-chloro-4-methylphenyl)-N,N-dimethylurea, N'-parachlorophenyl-N,N-dimethylurea, N-butyl-N'-(3,4-dichlorophenyl)-N-methylurea, N'-parachlorophenyl-O,N,N-trimethylisourea, N'-p-chlorophenyl-N-methoxy-N-methylurea, N,N-dimethyl-N'-phenylurea, 3-(4-bromophenyl)-1-methoxy-1-methylurea, 1-(2-benzothiazolyl)-3-methylurea, N,N-dimethyl-N'-(4-[1-methylethyl]phenyl)urea, N'-(3,4-dichlorophenyl)-N-methoxy-N-methylurea or N,N-dimethyl-N'-[3-(trifluoromethyl)phenyl]urea.

The triazine herbicide generally comprises 2-chloro-4-(1-cyano-1-methylamino)-6-ethylamino-1,3,5-triazine or 2-isopropylamino-4-(3-methoxypropylamino)-6-methylthio-1,3,5-triazine or a compound of the formula:

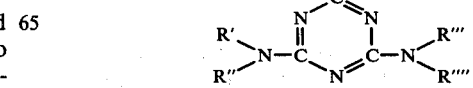

where X is a halogen atom, alkoxy or alkylthio, R' and R" are the same or different and are hydrogen or alkyl and R'" and R"" are the same or different alkyl groups, such as 2-chloro-4,6-bisethylamino-1,3,5-triazine, 2-chloro-4-ethylamino-6-diethylamino-1,3,5-triazine, 2-chloro-6-ethylamino-4-isopropylamino-1,3,5-triazine or 2,4-bis(isopropylamino)-6-methylthio-1,3,5-triazine.

The phenol herbicide generally comprises 4,6-dinitro-o-cresol, 4,6-dinitro-2-sec-butylphenol or pentachlorophenol. The nitrile herbicide generally comprises 3,5-diiodo-4-hydroxybenzonitrile, 3,5-dibromo-4-hydroxybenzonitrile or 2,6-dichlorobenzonitrile. The bipyridylium herbicide generally comprises 1,1'-dimethyl-4,4'-bipyridylium dichloride or 1,1'-ethylene-2,2'-bipyridylium dibromide. The substituted benzoic acid herbicide generally comprises 2,3,6-trichlorobenzoic acid, 2-methoxy-3,6-dichlorobenzoic acid or N-(1,1-dimethylpropynyl)-3,5-dichlorobenzamide. The halogenated aliphatic acid herbicide generally comprises trichloroacetic acid or 2,2-dichloropropionic acid. The carbamate herbicide generally comprises isopropyl N-(3-chlorophenyl) carbamate, 4-chloro-2-butynyl N-(3-chlorophenyl)carbamate, methyl 3-(m-tolylcarbamoyloxy)phenylcarbamate or D-N-ethyl-2-(phenylcarbamoyloxy)propionamide. The thiocarbamate herbicide generally comprises S-ethyl N,N-dipropylthiocarbamate, S-ethyl N,N-diisobutylthiocarbamate, S-(2,3-dichloroallyl) N,N-diisopropylthiocarbamate, S-ethyl N-ethyl-N-cyclohexylthiocarbamate, S-propyl butylethylthiocarbamate or S-(2,3,3-trichloroallyl) N,N-diisopropylthiocarbamate. The chloroacetamide herbicide generally comprises N,N-diallyl-2-chloroacetamide or N-isopropyl-2-chloroacetanilide. The diazine herbicide generally comprises 5-bromo-6-methyl-3-sec-butyluracil, 3-cyclohexyl-5,6-trimethyleneuracil, 5-amino-4-chloro-2-phenyl-3-pyridazinone or 1,2-dihydropyridazine-3,6-dione. The arsenic herbicide generally comprises a salt of methane arsonic acid or cacodylic acid. Other herbicides which may be used as the second herbicide include 1,2-dimethyl-3,5-diphenylpyrazolium ion, ethyl N-benzoyl-N-(3,4-dichlorophenyl)alanine, N-isobutyl-2-oxo-1-imidazolidine-carboxamide, aminotriazole, 2,3-dichloro-1,4-naphthoquinone, 4-amino-3,5,6-trichloropicolinic acid, N,N-dimethyl-2,2-diphenylacetamide, 2,6-dinitro-N,N-dipropyl-4-trifluoromethylaniline, N-butyl-N-ethyl-2,6-dinitro-4-trifluoromethylaniline, S,S,S-tributyl phosphorotrithioate, 2-ethoxy-2,3-dihydro-3,3-dimethyl-5-benzofuranyl methylsulphonate, 4-chloro-2-oxobenzothiazolin-3-yl acetic acid, 3-isopropyl-2,1,3-benzothiadiazinon-(4)-2,2-dioxide, 3,5-dibromo-4-hydroxybenzaldehyde 2,4-dinitrophenyloxime, methyl 2-chloro-3-(4-chlorophenyl)propionate, 2-chloroethyltrimethylammonium chloride, isopropyl 2-(N-benzoyl-3-chloro-4-fluoroanilino)propionate, methyl 2-(N-benzoyl-3-chloro-4-fluoroanilino)propionate, 2-chloro-N-(1,3-dioxolan-2-ylmethyl)-2',6'-dimethylacetanilide, 2-chloro-1-(3-ethoxy-4-nitrophenoxy)-4-trifluoromethylbenzene, methyl 2-(4-[2',4'-dichlorophenoxy]phenoxy)propionate or isobutyl 2-(4-[4'-chlorophenoxy]-phenoxy)propionate.

The other herbicide may particularly be another herbicide which combats wild oats in cereal crops.

The particular embodiments, the present compound and particularly one specified above as being preferred for use as a herbicide, e.g. N-cyano-methyl-3,4-dichloro-methanesulphonanilide, is used (a) in admixture with 4-chloro-2-butynyl 3-chlorophenylcarbamate, 1,2-dimethyl-3,5-diphenylpyrazolium ion, alpha-2-methyl-4-chlorophenoxypropionic acid, N'-(3-chloro-4-methoxyphenyl)-N,N-dimethylurea, N'-(3-chloro-4-methylphenyl)-N,N-dimethylurea or ethyl N-benzoyl-N-(3,4-dichlorophenyl)alanine, or (b) after emergence of the crop following use before emergence of the crop of S-2,3-dichloroallyl di-isopropylthiocarbamate or S-2,3,3-trichloroallyl di-isopropylthiocarbamate.

The present compound may be used in admixture or sequence with another fungicide, particularly another cereal fungicide. The other fungicide may be for instance one or more of maneb (polymeric manganese ethylenebisdithiocarbamate), zineb (zinc ethylenebisdithiocarbamate), mancozeb (which can be regarded as a mixture of maneb and zineb), thiram (tetramethylthiuram disulphide), ditalimfos (O,O-diethyl phthalimidophosphonothioate), tridemorph (2,6-dimethyl-4-tridecylmorpholine), fluotrimazole (1-[diphenyl(3-trifluoromethylphenyl)methyl]-1,2,4-triazole), ethirimol (5-butyl-2-ethylamino-4-hydroxy-6-methylpyrimidine), triforine (1,4-di[2,2,2-trichloro-1-formamidoethyl]piperazine), pyracarbolid (3,4-dihydro-6-methylpyran-5-carboxanilide), zineb-ethylene thiuramdisulphide adduct, carbendazim (methyl benzimidazol-2-ylcarbamate), captafol (3a,4,7,7a-tetrahydro-N-[1,1,2,2-tetrachloroethanesulphenyl]phthalimide), thiophanate (1,2-di[3-ethoxycarbonyl-2-thioureido]benzene), propineb (polymeric zinc propylenebisdithiocarbamate), oxycarboxin (2,3-dihydro-6-methyl-5-phenylcarbamoyl-1,4-oxathiin 4,4-dioxide), quintozene (pentachloronitrobenzene), benomyl (methyl 1-[butylcarbamoyl]benzimidazol-2-ylcarbamate), benadanil (2-iodobenzanilide), dichlofluanid (N-dichlorofluoromethanesulphenyl-N',N'-dimethyl-N-phenylsulphamide), sulphur, copper compounds, iprodione (3-[3,5-dichlorophenyl]-1-[(1-methylethyl)aminocarbonyl]-imidazolidine-2,4-dione, ziram (zinc dimethyldithiocarbamate), nabam (disodium ethylenebisdithiocarbamate), and triadimefon (1-(4-chlorophenoxy)-3,3-dimethyl-1-(1,2,4-triazol-1-yl)-2-butanone).

In a particular embodiment, the present compound, e.g. N-2-oxopropyl-2',6'-dimethyl-methanesulphonanilide, is used in admixture with thiram.

The present compound may be used in admixture or sequence with an insecticide, particularly a cereal insecticide. The insecticide may be for instance one or more of demeton-S-methyl (S-2-ethylthioethyl O,O-dimethyl phosphorothioate), dimethoate (O,O-dimethyl S-methylcarbamoylmethyl phosphorodithioate), formothion (S-[N-formyl-N-methylcarbamoylmethyl]O,O-dimethyl phosphorodithioate), oxydemeton-methyl (S-2-ethylsulphinylethyl O,O-dimethyl phosphorothioate), pirimicarb (2-dimethylamino-5,6-dimethylpyrimidin-4-yl dimethylcarbamate), thiometon (S-2-ethylthioethyl O,O-dimethyl phosphorodithioate), BHC (benzene hexachloride), aldrin (1,2,3,4,10,10-hexachloro-1,4a,5,8,8a-hexahydro-exo-1,4-endo-5,8-dimethanonaphthalene), fenitrothion (O,O-dimethyl O-4-nitro-m-tolyl phosphorothioate), omethoate (O,O-dimethyl S-methylcarbamoylmethyl phosphorothioate), pirimiphos-methyl (O-2-diethylamino-6-methyl-pyrimidin-4-yl O,O-dimethyl phosphorothioate) and DDT (1,1,1-trichloro-2,2-di[chlorophenyl]ethane).

The ratio of the present compound to the other pesticide or plant growth regulant may vary over a wide range according to the particular compounds involved and the intended use. In general, the ratio of present compound to other pesticide or plant growth regulant lies in the range 1:0.1 to 1:15.

The present compounds may be in admixture with non-phytotoxic oils, e.g. Agri-Oil Plus, Sun Oil 11E or Fyzol 11E.

The compounds may be in admixture with an antidote (a substance having the property of improving the selectivity of herbicides), e.g. N,N-diallyl-2,2-dichloroacetamide or 1,8-naphthalic anhydride.

The compounds may be in admixture with fertilizers.

In the use of the present compounds as total herbicides, high rates of application, for example at least 10 kg per hectare, such as 10-25 kg per hectare, of the compounds are usually required, unless they are mixed with other herbicides, in which case the rate can be reduced.

In the use of the present compounds as selective herbicides, the rate of application is usually much lower and may be for example 0.5-10, e.g 0.5-8, kg per hectare, such as 1-4 kg per hectare.

In the use of the compounds as plant growth regulants, low rates of application are usually required such as 0.1-4, eg 0.5-1, kg per hectare.

For use as fungicides, insecticides or anti-bacterial agents, the compounds are generally applied at a rate of 0.3-10, e.g. 1-6, kg per hectare. For use as fungicides, the compounds can be incorporated into a plant growing medium, particularly a peat based plant growing medium, in which plants are to grow, e.g. at a rate of 10-1000, preferably 50-500, g of compound per cubic meter. The compounds can be employed as seed dressings, 'seeds' being used in its wider sense as including tubers and bulbs; for this use, the compounds can be employed at a rate for example of 0.1-1 g per kg of seed and are preferably used in admixture with a carrier to facilitate admixture with the seed; the carrier can be a liquid, e.g. a hydrocarbon, or a solid, e.g. a clay or Fullers earth.

The present compounds may be applied to plants (including seeds), the soil (including compost), land or aquatic areas, or to inanimate or stored materials, e.g. textiles, paper, leather or wood, susceptible to fungal attack. They are preferably used as herbicides, particularly selective herbicides, or fungicides, especially for application to a locus at which a crop e.g. a food crop and especially a cereal crop such as wheat, barley or maize is growing or, less preferably, is to grow. Thus, the compounds may be applied pre- or post-planting of the crop. They may be employed for pre-emergence use or post-emergence use. The compounds may be used to protect plants from weeds and fungus.

The invention is illustrated by the following Examples, in which temperatures are in degrees C.

EXAMPLE 1

A solution of 1-propanesulphonyl chloride (25 ml) in toluene (50 ml) was added during 15 minutes to a stirred solution of 2,6-dimethylaniline (55 ml) in toluene (400 ml). The mixture was stirred and boiled under reflux for 20 hours, then cooled and filtered. The toluene solution was washed with dilute hydrochloric acid (3 times) and water, then extracted (3 times) with dilute sodium hydroxide solution. The aqueous alkaline solution was acidified with dilute hydrochloric acid, and the product collected by filtration, washed with water and dried. Crystallisation from toluene/60°-80° petrol gave 2',6'-dimethyl-1-propanesulphonanilide as buff coloured crystals (28.0 g, 55%), melting point 72°.

EXAMPLE 2

A mixture of the sulphonanilide of Example 1 (28.0 g), anhydrous potassium carbonate (9.4 g), ethyl 2-bromopropionate (17.6 ml) and 1,2-dimethoxyethane (200 ml) was stirred and boiled under reflux for 20 hours, then cooled and filtered, and the filtrate evaporated. A solution of the residual oil in ether was washed with dilute sodium hydroxide solution. The alkaline solution was acidified with dilute hydrochloric acid and the precipitated solid was collected by filtration. This material (13.3 g) was identified as unreacted sulphonanilide. The ethereal solution was evaporated and a solution of the residual oil in ethanol/10% sodium hydroxide solution (100 ml, 1:1) was heated at 50° for 2 hours. The ethanol was evaporated, leaving an aqueous solution of the sodium salt of N-(2,6-dimethylphenyl)-N-(1-propanesulphonyl)-alanine. The solution was acidified with dilute hydrochloric acid. The product acid was extracted with chloroform, the chloroform solution was dried and evaporated, and the residue crystallised from toluene/60°-80° petrol to give buff coloured crystals of N-(2,6-dimethylphenyl)-N-(1-propanesulphonyl)alanine (14.1 g) (73% yield based on unrecovered sulphonanilide).

EXAMPLE 3

A solution of the alanine derivative of Example 2 (6.5 g) in toluene (100 ml) was treated with thionyl chloride (10 ml), boiled under reflux for 1 hour, then evaporated. The residual oil was re-evaporated with toluene to remove traces of thionyl chloride, and the residue was then boiled in 2-propanol for 1 hour and evaporated. A solution of this oily residue in ether was washed with sodium bicarbonate solution, dried and evaporated to a brown oil which was percolated through a column of silica gel with chloroform. Evaporation of the eluate gave the isopropyl ester

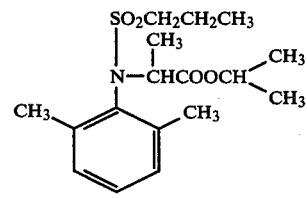

as a clear yellow oil;

Analysis: Found: 59.45%C, 7.91%H, 3.77N. $C_{17}H_{27}NO_4S$ requires: 59.79%C, 7.97%H, 4.10%N.

EXAMPLES 4-33

Following an analogous procedure to that of the previous Examples, the following compounds were prepared:

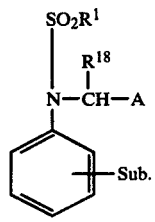

Acids

| Example | R$^1$ | R$^{18}$ | A | Sub | Melting Point |
|---|---|---|---|---|---|
| 4 | Me | Me | COOH | 3,4-diCl | 131° |
| 5 | Me | Me | COOH | 2-Et | 212° |
| 6 | Me | Me | COOH | 2-Cl—6Me | 98° |
| 7 | Me | Me | COOH | 2,6-diMe | 118° |
| 8 | Me | Me | COOH | 2-OCH$_3$ | 131° |
| 9 | Et | Me | COOH | 2,6-diMe | 122° |
| 10 | Me | Me | COOH | 2,6-diEt | 118° |
| 11 | Me | Me | COOH | 2,6-diCl | 128° |

Esters

| Example | R$^1$ | R$^{18}$ | A | Sub | Melting Point | Found / Requires | % C | % H | % N |
|---|---|---|---|---|---|---|---|---|---|
| 12 | Me | H | COOEt | 4-Cl | Oil | Found | 45.03 | 4.63 | 4.74 |
|    |    |   |       |      |     | C$_{11}$H$_{14}$ClNO$_4$S | 45.28 | 4.84 | 4.80 |
| 13 | Me | Me | COOEt | 4-Cl | Oil | Found | 46.82 | 5.45 | 4.78 |
|    |    |    |       |      |     | C$_{12}$H$_{16}$ClNO$_4$S | 47.13 | 5.27 | 4.58 |
| 14 | Me | H | COOEt | 2,6-diMe | Oil | Found | 54.62 | 6.51 | 5.17 |
|    |    |   |       |          |     | C$_{13}$H$_{19}$NO$_4$S | 54.72 | 6.71 | 4.91 |
| 15 | Me | Me | COOEt | 2,6-diMe | Oil | Found | 56.04 | 7.29 | 5.07 |
|    |    |    |       |          |     | C$_{14}$H$_{21}$NO$_4$S | 56.16 | 7.07 | 4.68 |
| 16 | Me | Me | COOEt | 3-CF$_3$ | Oil | Found | 45.84 | 5.00 | 4.37 |
|    |    |    |       |          |     | C$_{13}$H$_{16}$F$_3$NO$_4$S | 46.01 | 4.75 | 4.13 |
| 17 | Me | H | COOEt | 3-CF$_3$ | Oil | Found | 44.00 | 4.11 | 4.61 |
|    |    |   |       |          |     | C$_{12}$H$_{14}$F$_3$NO$_4$S | 44.30 | 4.34 | 4.31 |
| 18 | Me | H | COOEt | 3,4-diCl | Oil | Found | 40.78 | 3.96 | 4.59 |
|    |    |   |       |          |     | C$_{11}$H$_{13}$Cl$_2$NO$_4$S | 40.50 | 4.02 | 4.29 |
| 19 | Me | H | COOEt | 2-isoPr | Oil | Found | 55.99 | 7.38 | 4.96 |
|    |    |   |       |         |     | C$_{14}$H$_{21}$NO$_4$S | 56.16 | 7.07 | 4.68 |
| 20 | Me | Me | COOEt | 3,4-diCl | Oil | Found | 41.90 | 3.99 | 4.60 |
|    |    |    |       |          |     | C$_{12}$H$_{15}$Cl$_2$NO$_4$S | 42.36 | 4.44 | 4.12 |
| 21 | Me | Me | COOEt | 2-Et | Oil | Found | 55.94 | 6.89 | 4.88 |
|    |    |    |       |      |     | C$_{14}$H$_{21}$NO$_4$S | 56.16 | 7.07 | 4.68 |
| 22 | Me | Me | COOEt | 2-Cl,6Me | Oil | Found | 48.52 | 5.43 | 4.33 |
|    |    |    |       |          |     | C$_{13}$H$_{18}$ClNO$_4$S | 48.82 | 5.67 | 4.38 |
| 23 | Me | Me | COOEt | 2-OCH$_3$ | Oil | Found | 52.19 | 6.36 | 4.84 |
|    |    |    |       |           |     | C$_{13}$H$_{19}$NO$_5$S | 51.81 | 6.36 | 4.65 |
| 24 | n-Pr | Me | COOEt | 2,6-diMe | 44–46° | Found | 58.28 | 7.77 | 4.11 |
|    |      |    |       |          |        | C$_{16}$H$_{25}$NO$_4$S | 58.69 | 7.70 | 4.28 |
| 25 | Me | Me | COOEt | 2-Cl | Oil | Found | 47.05 | 5.60 | 4.80 |
|    |    |    |       |      |     | C$_{12}$H$_{16}$ClNO$_4$S | 47.14 | 5.27 | 4.58 |
| 26 | Et | Me | COOEt | 2,6-diMe | 70° | Found | 57.83 | 7.77 | 4.33 |
|    |    |    |       |          |     | C$_{15}$H$_{23}$NO$_4$S | 57.48 | 7.40 | 4.42 |
| 27 | n-Bu | Me | COOEt | 2,6-diMe | Oil | Found | 59.45 | 8.25 | 3.83 |
|    |      |    |       |          |     | C$_{17}$H$_{27}$NO$_4$S | 59.79 | 7.97 | 4.10 |
| 28 | Me | Me | COOEt | 2,6-diCl | 108° | | | | |
| 29 | Me | Me | COOMe | 2,6-diMe | Oil | Found | 54.69 | 6.69 | 4.46 |
|    |    |    |       |          |     | C$_{13}$H$_{19}$NO$_4$S | 54.72 | 6.71 | 4.91 |
| 30 | Me | Me | COOEt | 2,6-diEt | Oil | Found | 59.00 | 7.35 | 4.59 |
|    |    |    |       |          |     | C$_{16}$H$_{25}$NO$_4$S | 58.69 | 7.70 | 4.28 |
| 31 | Me | Me | COOn-Pr | 2,6-diMe | Oil | Found | 57.57 | 7.49 | 4.41 |
|    |    |    |         |          |     | C$_{13}$H$_{23}$NO$_4$S | 57.48 | 7.40 | 4.47 |
| 32 | Me | Me | COO(CH$_2$)$_4$CH$_3$ | 2,6-diMe | Oil | Found | 59.66 | 8.10 | 3.98 |
|    |    |    |                       |          |     | C$_{17}$H$_{27}$NO$_4$S | 59.79 | 7.97 | 4.10 |
| 33 | Me | Me | COOCHCH$_3$<br>\|<br>(CH$_2$)$_5$CH$_3$ | 2,6-diMe | Oil | Found | 63.01 | 8.51 | 3.70 |
|    |    |    |                                          |          |     | C$_{20}$H$_{33}$NO$_4$S | 62.63 | 8.67 | 3.65 |

EXAMPLE 34

A solution of N-(2,6-dimethylphenyl)-N-methanesulphonyl alanine (5 g) in chloroform (50 ml) was treated with thionyl chloride (5 ml), and the solution was boiled under reflux for 1 hour then evaporated. The residue was re-evaporated with toluene to remove traces of thionyl chloride. A chloroform solution of the residue was treated with a saturated solution of ammonia in chloroform, the mixture was allowed to stand at room temperature for 4 hours, then water was added and the organic solvent evaporated. The suspended solid was removed by filtration, washed with water and dried. Recrystallisation from ethanol gave the amide

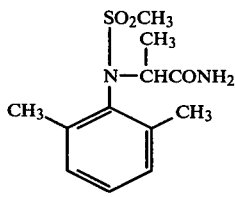

as colourless crystals, melting point 158°.

EXAMPLES 35–43

Following an analogous procedure to that of Example 34, the following compounds were prepared:

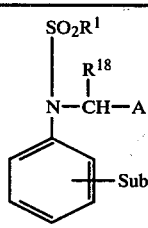

| Example | $R^1$ | $R^{18}$ | A | Sub | Melting Point |
|---|---|---|---|---|---|
| 35 | Me | H | $CONEt_2$ | 4-Cl | 76° |
| 36 | Me | H | $CONEt_2$ | 2,6-diMe | 76° |
| 37 | Me | H | $CONEt_2$ | 2-isoPr | 108° |
| 38 | Me | H | $CONEt_2$ | 3-$CF_3$ | 54° |
| 39 | Me | H | $CONEt_2$ | 3,4-diCl | 90° |
| 40 | Me | Me | CONHPh | 2-Et | 156° |
| 41 | Me | Me | CON⟨O⟩ | 2-Et | 120° |
| 42 | Me | Me | $CONH_2$ | 2,6-diEt | 134° |
| 43 | Me | Me | $CONH_2$ | 2-Cl,6-Me | 158° |

EXAMPLE 44

A mixture of 3,4-dichloro-methanesulphonanilide (7.0 g), anhydrous potassium carbonate (2.4 g), chloroacetonitrile (2.2 ml) and 1,2-dimethoxyethane (100 ml) was stirred and boiled under reflux for 6 hours. The dark coloured reaction mixture was cooled, filtered and evaporated. A solution of the residual oil in chloroform was washed well with water, dried, and evaporated to give a black oil which was percolated through a column of silica gel with chloroform. Evaporation of the eluate gave an oil, a solution of which in ethanol deposited a cream coloured solid identified as N-cyanomethyl-3,4-dichloro-methanesulphonanilide (3.8 g), melting point 83°,

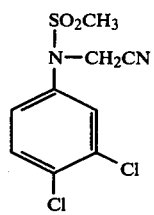

EXAMPLES 45–48

Following an analogous procedure to that of Example 44, the following compounds were prepared:

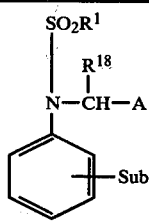

| Example | $R^1$ | $R^{18}$ | A | Sub | Melting Point |
|---|---|---|---|---|---|
| 45 | Me | H | CN | 4-Cl | 102° |
| 46 | Me | H | CN | 2,6-diMe | 84° |
| 47 | Me | H | CN | 2-isoPr | 99° |
| 48 | Me | H | CN | 3-$CF_3$ | 61° |

EXAMPLES 49–55

Seeds of the plant species listed below were sown in anodised aluminium pans, 19 cm long×9.5 cm wide×5 cm deep, containing John Innes I potting compost. They were then watered and placed in a controlled environment room (22° C.; 65–85% relative humidity; 14 hours per day artificial illumination at 13,000 lux). Fourteen days after sowing, the seedlings received a foliar spray of a compound listed below, formulated as a solution in 1:1 by volume aqueous acetone. The concentration of active ingredient and volume of application were adjusted so as to be equivalent to a rate of 11.2 kg/ha in 450 liters per hectare. After seven days growth in the controlled environment room, the plants were visually assessed for any herbicidal or growth regulant response. All differences from the untreated control were scored according to an index where 0=no effect and 100=complete kill. The results are shown in the following table:

| Species | | Example | 49 | 50 | 51 | 52 | 53 | 54 | 55 |
|---|---|---|---|---|---|---|---|---|---|
| | | Compound of Example | 15 | 22 | 3 | 24 | 25 | 26 | 27 |
| | | Dosage rate kg/ha - | 11.2 | 11.2 | 11.2 | 11.2 | 11.2 | 11.2 | 11.2 |
| Peas | (*Pisum sativum*) | | 5 | 5 | 5 | 20 | 5 | 5 | 5 |
| Mustard | (*Sinapis alba*) | | 90 | 80 | 90 | 100 | 80 | 100 | 100 |
| Linseed | (*Linum usitatissimum*) | | 90 | 30 | 30 | 90 | 20 | 100 | 70 |
| Ryegrass | (*Lolium perenne*) | | 10 | 5 | 15 | 75 | 0 | 40 | 20 |
| Sugarbeet | (*Beta vulgaris*) | | 90 | 80 | 90 | 90 | 30 | 90 | 90 |
| Oat | (*Avena sativa*) | | 5 | 5 | 5 | 30 | 20 | 40 | 30 |
| French beans | (*Phaseolus vulgaris*) | | 70 | 80 | 80 | 100 | — | — | — |

EXAMPLES 56-60

The compounds listed below were each formulated as an attaclay/sand dust and incorporated into John Innes I potting compost at a rate equivalent to 26 parts per million weight/volume of active ingredient to soil and placed in anodised aluminium pans, 19 cm long×9.5 cm wide×5.0 cm deep. This rate is approximately equivalent to a soil surface application of 11.2 kg active ingredient/hectare cultivated to a depth of 5 cm. Seeds of the species listed below were sown in the treated soil, watered and placed in a controlled environment room (22° C.; 65-85% relative humidity; 14 hours per day artificial illumination at 13,000 lux) for 21 days. The plants were then visually assessed for any growth regulatory or herbicidal effects. All differences from an untreated control were scored on a scale from 0–100, where 0 signifies no effect and 100 signifies complete kill. The results are shown in the following table:

| Species | Example Compound of Example Dosage rate (ppm) | 56 15 26 | 57 44 26 | 58 22 26 | 59 3 26 | 60 24 26 |
|---|---|---|---|---|---|---|
| Peas | (Pisum sativum) | 0 | 0 | 0 | 0 | 0 |
| Mustard | (Sinapis alba) | 100 | 40 | 100 | 90 | 100 |
| Linseed | (Linum usitatissimum) | 70 | 20 | 100 | 20 | 100 |
| Maize | (Zea mays) | 50 | 5 | 50 | 20 | 60 |
| Oats | (Avena sativa) | 20 | 60 | 50 | 20 | 60 |
| Ryegrass | (Lolium perenne) | 100 | 5 | 90 | 90 | 100 |

EXAMPLES 61-65

Seeds of the plant species listed below were sown in John Innes I potting compost in aluminium pans, 19 cm long×9.5 cm wide×5.0 cm high, one species per pan. The soil surface was then sprayed with a compound listed below, formulated as a solution in 1:1 by volume aqueous acetone except for the compound of Example 44 which was formulated as an aqueous suspension containing 1000 parts per million of the wetting agent Lissapol NX (nonylphenol/ethylene oxide condensate). Each compound was applied at a rate of 2.8 kg of active ingredient per hectare in 450 liters of spray liquid per hectare. The pans were then watered, and placed in a controlled environment room (22° C., relative humidity 65-85%, 14 hours per day artificial illumination at 17,000 lux) for 21 days. The plants were then visually assessed for any growth regulatory or herbicidal effects. All differences from an untreated control were scored on a scale from 0–100, where 0 signifies no effect and 100 signifies complete kill. The results are shown in the following table:

| Species | Example Compound of Example Dosage rate kg/ka | 61 15 2.8 | 62 44 2.8 | 63 22 2.8 | 64 3 2.8 | 65 24 2.8 |
|---|---|---|---|---|---|---|
| Chickweed | (Stellaria media) | 30 | — | 50 | — | — |
| Mustard | (Sinapis alba) | 10 | — | 90 | — | — |
| Cotton | (Gossypium sp.) | 0 | — | 0 | — | — |
| Tomato | (Lycopersicon esculentum) | 20 | — | 40 | — | — |
| Fathen | (Chenopodium album) | 100 | — | 100 | — | — |
| Carrot | (Daucus carota) | 0 | — | 0 | — | — |
| Wheat | (Triticum aestivum) | 0 | 0 | 0 | 0 | 10 |
| Barley | (Hordeum vulgare) | 0 | 0 | 0 | 0 | 30 |
| Wild Oat | (Avena fatua) | 5 | 0 | 0 | 80 | 100 |
| Blackgrass | (Alopecurus myosuroides) | 20 | 0 | 40 | 90 | 100 |
| Barnyardgrass | (Echinochloa crus-galli) | 40 | 80 | 0 | 60 | 80 |
| Crabgrass | (Digitaria sanguinalis) | 100 | 0 | 90 | 90 | 100 |
| Rice | (Orysae sotiva) | — | 0 | — | — | — |

EXAMPLE 66

Seeds of the monocotyledon species listed below were sown in anodised aluminium pans, 19 cm long×9.5 cm wide×5.0 cm deep, containing John Innes I potting compost. They were then watered and placed in a controlled environment room (22° C.; 65-85% relative humidity; 14 hours per day artificial illumination at 17,000 lux). 14 days after sowing, the seedlings were given a foliar spray of the compound of Example 44, formulated as an aqueous suspension together with 2000 ppm of the wetting agent Lissapol NX. The dosage rate was adjusted to be 2.8 kg active ingredient in 450 liters per hectare. After a further 14 days in the controlled environment room, the plants were visually assessed for any growth regulatory or herbicidal effect. All differences from an untreated control were scored on a scale from 0-100 where 0 signifies no effect and 100 signifies complete kill. The results are shown in the following table:

| Species | | Dosage rate kg/ha 2.8 |
|---|---|---|
| Wheat | (Triticum aestivum) | 0 |
| Barley | (Hordeum vulgare) | 0 |
| Barnyardgrass | (Echinochloa crus-galli) | 100 |

EXAMPLES 67-83

The compounds listed below were tested according to the procedure of Examples 56-60 but at 130 parts per million weight/volume of active ingredient to soil. This rate is approximately equivalent to a soil surface application of 56 kg active ingredient per hectare cultivated to a depth of 5 cm.

The results are shown below:

| Species | Example Compound of Example | 67 4 | 68 5 | 69 7 | 70 9 | 71 12 | 72 14 | 73 17 | 74 18 | 75 25 | 76 26 | 77 27 | 78 35 | 79 36 | 80 45 | 81 46 | 82 47 | 83 48 |
|---|---|---|---|---|---|---|---|---|---|---|---|---|---|---|---|---|---|---|
| Peas | (Pisum sativum) | 70 | 30 | 20 | 50 | 40 | 30 | 40 | 40 | 5 | 100 | 20 | 20 | 20 | 20 | 20 | 10 | 50 |
| Mustard | (Sinapis alba) | 70 | 50 | 70 | 70 | 70 | 100 | 40 | 40 | 100 | 100 | 100 | 100 | 100 | 100 | 100 | 80 | 100 |
| Linseed | (Linum usitatissimum) | 90 | 70 | 50 | 80 | 80 | 90 | 90 | 80 | 50 | 100 | 100 | 40 | 40 | 90 | 90 | 100 | 100 |
| Ryegrass | (Lolium perenne) | 0 | 20 | 0 | 20 | 5 | 30 | 0 | 30 | 0 | 100 | 100 | 20 | 20 | 80 | 80 | 50 | 90 |
| Oats | (Avena sativa) | 40 | 30 | 30 | 20 | 5 | 20 | 0 | 0 | 20 | 100 | 100 | 20 | 20 | 70 | 70 | 30 | 80 |
| Maize | (Zea mays) | 70 | 30 | 30 | 30 | 0 | 40 | 0 | 30 | 40 | 100 | 100 | 20 | 20 | 30 | 30 | 10 | 40 |

EXAMPLE 84

Aqueous acetone suspensions containing 2000 mg of the compound of Example 15 per liter and 125 mg of the wetting agent Lissapol NX (nonylphenol/ethylene oxide condensate) per liter were applied to the soil surrounding the roots and leaves of cucumber plants with two fully expanded leaves. The treated plants, together with controls treated with wetting agent alone, were inoculated 24 hours after the chemical application with spores of the disease organism known as cucumber powdery mildew *Erysiphe cichoracearum*. The plants were then placed in a controlled environment room (18° C. and 80–90% relative humidity) until disease incidence was measured after fourteen days, when it was found that the treatment with active compound had given 82% fungus control, in comparison with less than 5% on the controls.

EXAMPLE 85

A slow stream of hydrogen sulphide gas was bubbled through a stirred solution of N-cyanomethyl-3,4-dichloromethanesulphonanilide (6.0 g) in pyridine (75 ml) containing triethylamine (11.0 ml). Reaction was carried out at room temperature for 4 hours, and the mixture was then poured into ice/water (1500 ml). The precipitated buff coloured solid was collected by filtration, washed with water, and dried. The product was identified as N-(thiocarbamoylmethyl)-3, 4-dichloromethanesulphonanilide (6.0 g, 89% yield), melting point 178°.

EXAMPLES 86–89

By following procedures analogous to that of Example 85, the following compounds were prepared:

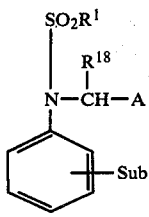

| Example | $R^1$ | $R^{18}$ | A | Sub | Melting Point |
|---|---|---|---|---|---|
| 86 | Me | H | $-\overset{S}{\underset{\parallel}{C}}NH_2$ | 2-isopropyl | 136° |
| 87 | Me | H | $-\overset{S}{\underset{\parallel}{C}}NH_2$ | 4-chloro | 186° |
| 88 | Me | H | $-\overset{S}{\underset{\parallel}{C}}NH_2$ | 3-$CF_3$ | 136° |
| 89 | Me | H | $-\overset{S}{\underset{\parallel}{C}}NH_2$ | 2,6-dimethyl | 160° |

EXAMPLES 90–92

Following an analogous procedure to that of Example 2, the following compounds were prepared:

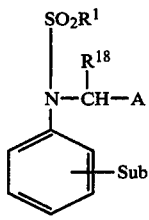

| Example | $R^1$ | $R^{18}$ | A | Sub | Melting Point |
|---|---|---|---|---|---|
| 90 | Me | Et | COOH | 2,6-diMe | 164° |
| 91 | n-Bu | Me | COOH | 2,6-diMe | 112° |
| 92 | n-Pr | Me | COOH | 2,6-diMe | 143° |

EXAMPLES 93–122

Following an analogous procedure to that of Example 3, the following compounds of the formula given in Examples 90–92 were prepared:

| Example | $R^1$ | $R^{18}$ | A | Sub | Melting Point | Found Requires | % C | % H | % N |
|---|---|---|---|---|---|---|---|---|---|
| 93 | Et | Me | $COOnC_4H_9$ | 2,6diMe | Oil | | 60.02 | 7.61 | 3.80 |
| | | | | | | $C_{17}H_{27}NO_4S$ | 59.79 | 7.97 | 4.10 |
| 94 | Me | H | COOEt | 2-Cl,6Me | Oil | | 46.79 | 4.90 | 4.37 |
| | | | | | | $C_{12}H_{16}ClNO_4S$ | 47.13 | 5.27 | 4.58 |
| 95 | Me | Et | COOEt | 2,6diMe | Oil | | 57.56 | 7.26 | 4.66 |
| | | | | | | $C_{15}H_{23}NO_4S$ | 57.48 | 7.40 | 4.47 |
| 96 | $NMe_2$ | Me | COOEt | 3,4-diCl | Oil | | 42.70 | 4.60 | 7.16 |
| | | | | | | $C_{13}H_{18}Cl_2N_2O_4S$ | 42.28 | 4.91 | 7.59 |
| 97 | Me | Me | COOEt | 4-$OSO_2$Me | 101° | | | | |
| 98 | 2-$NO_2$-phenyl | Me | COOEt | 2,6-diMe | 164° | | | | |
| 99 | thienyl | Me | COOEt | 3,4-diCl | 80–82° | | | | |

-continued

| Example | R¹ | R¹⁸ | A | Sub | Melting Point | Found Requires | %C | %H | %N |
|---|---|---|---|---|---|---|---|---|---|
| 100 | thienyl | Me | COOEt | 2,6-diMe | Oil | $C_{17}H_{21}NO_4S_2$ | 56.01 / 55.56 | 5.92 / 5.76 | 3.58 / 3.81 |
| 101 | NMe₂ | Me | COOEt | 2,6-diMe | Oil | $C_{15}H_{24}N_2O_4S$ | 55.04 / 54.85 | 7.00 / 7.37 | 8.36 / 8.53 |
| 102 | NMe₂ | Me | COOEt | 2-Cl,6-Me | Oil | $C_{14}H_{21}ClN_2O_4S$ | 48.05 / 48.20 | 5.68 / 6.07 | 7.94 / 8.03 |
| 103 | NMe₂ | Me | COOMe | 2-Cl,6-Me | Oil | $C_{13}H_{19}ClN_2O_4S$ | 46.95 / 46.63 | 5.39 / 5.72 | 7.91 / 8.37 |
| 104 | Me | Me | COOEt | 2-OSO₂Me | Oil | $C_{13}H_{19}NO_7S_2$ | 42.76 / 42.73 | 5.34 / 5.24 | 3.60 / 3.83 |
| 105 | NMe₂ | Me | COOMe | 2,6-diMe | 71° | | | | |
| 106 | Me | Me | COOEt | 4-OH | 108° | | | | |
| 107 | Me | Me | COOisoPr | 2,6-diMe | 64° | | | | |
| 108 | Me | Me | COO-cyclohexyl | 2-Cl,6Me | 76° | | | | |
| 109 | Me | Me | COOisoPr | 2-Cl,6Me | 78° | | | | |
| 110 | NMe₂ | H | COOEt | 3,4-diCl | Oil | $C_{13}H_{16}Cl_2N_2O_4S$ | 42.88 / 42.51 | 4.54 / 4.39 | 7.85 / 7.63 |
| 111 | Me | Me | COO-cyclohexyl | 2,6-diMe | 108° | | | | |
| 112 | NMe₂ | H | COOMe | 3,4diCl | Oil | $C_{11}H_{14}Cl_2N_2O_4S$ | 39.01 / 38.72 | 4.00 / 4.14 | 8.61 / 8.21 |
| 113 | NMe₂ | H | COOEt | 4-Cl | Oil | $C_{12}H_{17}ClN_2O_4S$ | 45.22 / 44.93 | 5.16 / 5.34 | 8.57 / 8.73 |
| 114 | Et | Me | COOisoPr | 2,6-diMe | Oil | $C_{16}H_{25}NO_4S$ | 59.02 / 58.69 | 7.95 / 7.70 | 4.61 / 4.28 |
| 115 | 2-NO₂-phenyl | Me | COOEt | 2-Cl,6Me | 142° | | | | |
| 116 | Et | Me | COO-cyclohexyl | 2,6-diMe | 92° | | | | |
| 117 | Me | H | —(CH₂)₂COOEt | 2,6-diMe | Oil | $C_{15}H_{23}NO_4S$ | 57.14 / 57.48 | 7.16 / 7.40 | 4.33 / 4.47 |
| 118 | Me | H | —(CH₂)₂COOMe | 2,6-diMe | Oil | $C_{14}H_{21}NO_4S$ | 55.81 / 56.16 | 6.94 / 7.07 | 4.50 / 4.68 |
| 119 | Me | H | —(CH₂)₂COOCH(CH₃)C₆H₁₃ | 2,6-diMe | Oil | $C_{21}H_{35}NO_4S$ | 63.80 / 63.447 | 8.44 / 8.87 | 3.83 / 3.52 |
| 120 | Me | Me | COOMe | 2-CF₃,4-SPh | Oil | $C_{18}H_{18}F_3NO_4S_2$ | 49.72 / 49.87 | 4.53 / 4.19 | 3.71 / 3.23 |
| 121 | Et | Et | COOEt | 2,6-diMe | Oil | $C_{16}H_{25}NO_4S$ | 58.29 / 58.69 | 7.40 / 7.70 | 3.94 / 4,28 |
| 122 | nPr | Et | COOEt | 2,6-diMe | 51° | | | | |

EXAMPLE 123

Following an analogous procedure to that of Example 2 but employing bromolactone starting material, the lactone

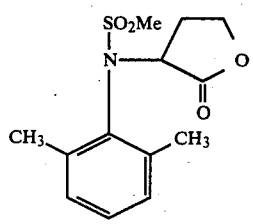

melting point 127°, was prepared.

EXAMPLES 124–127

Following an analogous procedure to that of Example 34, the following compounds of formula given in Examples 90–92 were prepared:

| Example | R¹ | R¹⁸ | A | Sub | Melting Point | Analysis where Product is an Oil ANALYSIS Found Requires | % C | % H | % N |
|---------|-----|------|-----------------------|-----------|---------------|---------------------------------------------------------|-------|------|------|
| 124 | Me | H | CONEt₂ | 2-Cl,6-Me | 70° | | | | |
| 125 | Me | Me | CONHCH₂COOEt | 2,6-diMe | 99° | | | | |
| 126 | Me | Me | CONHNHCOOEt | 2,6-diMe | 178° | | | | |
| 127 | Me | H | CH₂CH₂CONEt₂ | 2,6-diMe | Oil | C₁₇H₂₈N₂O₃S | 59.86 59.97 | 8.64 8.29 | 8.40 8.23 |

EXAMPLES 128–148

Following an analogous procedure to that of Example 44, the following compounds of formula given in Examples 90–92 were prepared:

| Example | R¹ | R¹⁸ | A | Sub | Melting Point |
|---------|------|-----|-----------|-----------|---------------|
| 128 | Me | H | CN | 2-Cl,6Me | 68° |
| 129 | Me | Me | CN | 2,6-diMe | 80–82° |
| 130 | Me | H | CN | 2-Cl | 65° |
| 131 | Me | H | CN | 3-Cl,4Me | 88° |
| 132 | nPr | H | CN | 3,4-diCl | 80° |
| 133 | Me | H | CN | 2,5-diCl | 112° |
| 134 | Me | H | CN | 3-Cl,4-F | 110° |
| 135 | Me | H | CN | 2,6-diCl | 82° |
| 136 | Me | H | CN | 2-OSO₂Me | 98–99° |
| 137 | Et | H | CN | 3,4-diCl | 79–81° |
| 138 | NMe₂ | H | CN | 3,4-diCl | 85° |
| 139 | Me | H | CN | 2,3-diCl | 86° |
| 140 | Me | H | CN | 3-Cl | 64° |
| 141 | Me | H | CN | 4-SCN | 118° |
| 142 | Me | H | CN | 3-NO₂,4-Cl | 114–116° |
| 143 | Me | H | CN | 2,4-diCl | 88° |
| 144 | NMe₂ | H | CN | 4-Cl | 52° |
| 145 | Me | H | CN | 3,4-diMe | 102° |
| 146 | Me | H | —(CH₂)₂CN | 2,6-diMe | 51° |
| 147 | Me | H | —(CH₂)₂CN | 3,4-diCl | 78° |
| 148 | Me | H | —(CH₂)₂CN | 3,4-diMe | 88° |

EXAMPLES 149–160

Following an analogous procedure to that of Example 85, the following compounds of formula given in Examples 90–92 were prepared:

| Example | R¹ | R¹⁸ | A | Sub | Melting Point |
|---------|-----|-----|-------|-----------|---------------|
| 149 | Me | H | CSNH₂ | 2-Cl,6Me | 152° |
| 150 | Me | H | CSNH₂ | 3-Cl,4Me | 202° |
| 151 | Me | H | CSNH₂ | 2-Cl | 172° |
| 152 | Me | H | CSNH₂ | 2,6-diCl | 180° |
| 153 | Me | H | CSNH₂ | 2,5-diCl | 196° |
| 154 | Me | H | CSNH₂ | 3-Cl | 184° |
| 155 | nPr | H | CSNH₂ | 3,4-diCl | 168–170° |
| 156 | Et | H | CSNH₂ | 3,4-diCl | 162–164° |
| 157 | Me | H | CSNH₂ | 2,3-diCl | 178° |
| 158 | Me | H | CSNH₂ | 3-Cl,4-F | 182° |
| 159 | Me | H | CSNH₂ | 2,4-diCl | 160° |
| 160 | Me | H | CSNH₂ | 2-OSO₂Me | 180° |

EXAMPLE 161

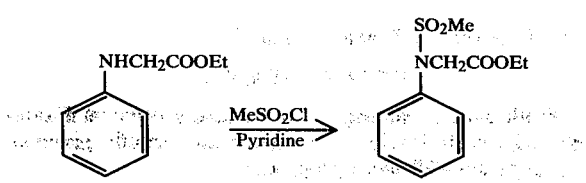

A solution of N-phenylglycine ethyl ester (10.0 g) in pyridine (50 ml) was treated with methane sulphonyl chloride (4.3 ml). The exothermic reaction was allowed to proceed unchecked, then the mixture was boiled under reflux for 2½ hours, cooled and poured into a rapidly stirred mixture of ice/water/hydrochloric acid. The precipitated, buff coloured, solid was collected by filtration, washed with water and dried. Yield 7.0 g (49%). Recrystallisation from ethyl acetate/60°–80° petrol gave colourless crystals of melting point 66°.

EXAMPLE 162

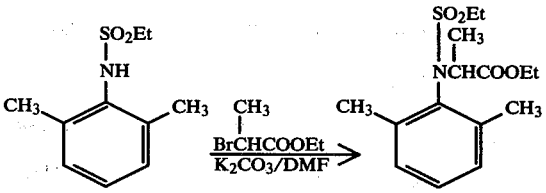

A mixture of 2',6'-dimethylethanesulphonanilide (6.0 g), anhydrous potassium carbonate (2.1 g), ethyl 2-bromopropionate (3.65 ml) and dimethylformamide (DMF) (90 ml) was stirred and heated at 90° for 7½ hours. The mixture was cooled, filtered, the residue washed on the filter with hot DMF, and the filtrate evaporated. The resulting yellow oil was dissolved in ether and the solution washed successively with 10% sodium hydroxide solution and water, then dried (MgSO₄) and evaporated. The solid residue was slurried with a little ethanol and the crystals collected by filtration. Yield of N-1-carboethoxyethyl-2',6'-dimethyl-ethanesulphonanilide was 5.7 g (65%). Melting point 70°.

EXAMPLE 163

A mixture of 2',6'-dimethylethanesulphonanilide (68.5 g), anhydrous potassium carbonate (24.5 g), ethyl 2-bromopropionate (58.0 g) and 1,2-di-methoxyethane (400 ml) was stirred and boiled under reflux for 66 hours, then cooled, filtered and the filtrate evaporated.

A solution of the oily residue in ether was washed 3 times with 10% sodium hydroxide solution (100 ml), washed with water, dried (MgSO₄) and evaporated to give N-(1-carboethoxyethyl)-2',6'-dimethylethanesulphonanilide as a pale yellow oil having purity greater than 99% (by gas-liquid chromatography).

Analysis

| Empirical Formula | C₁₅ | H₂₃ | N | O₄ | S |
|-------------------|-------|------|------|-------|-------|
| Theory, % | 57.48 | 7.40 | 4.47 | 20.42 | 10.23 |
| Found, % | 57.19 | 7.71 | 4.81 | | |

The aqueous alkali washes were combined, and acidified with dilute HCl. The precipitated solid (9.9 g) was filtered off, washed with water, dried and identified as recovered unreacted sulphonanilide.

Total yield of the ester was 84.5 g (98% yield based on sulphonanilide not recovered).

EXAMPLE 164

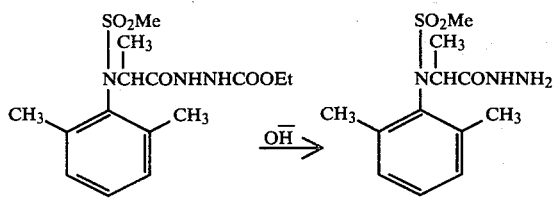

A solution of the N-[1-(2-ethoxycarbonyl)hydrazinocarbonyl)ethyl]-2',6'-dimethylmethane sulphonanilide (5.6 g) in ethanol (75 ml) plus 10% NaOH solution (75 ml) was heated on a steam bath for 2½ hours and then cooled, and the ethanol evaporated. The resultant aqueous solution was acidified, heated on the steam bath for 1 hour, and then filtered. The filtrate was just neutralised with dilute NaOH, saturated with sodium chloride, and extracted with chloroform. The chloroform solution was dried and evaporated. The residue gave almost colourless crystals of N-(1-hydrazinocarbonyl)ethyl)-2',6'-dimethylmethanesulphonanilide from a solution in toluene/60°-80° petrol. Yield 2.6 g (58%). Melting point 115°-118°.

EXAMPLE 165

In a standard test indicative of insecticidal activity, 30% inhibition of acetylcholinesterase was exhibited by the compound N-[2-(methylcarbamyloxyimino)-propyl]-2',6'-dimethyl-methanesulphonanilide at a 100 micromolar concentration of compound.

EXAMPLE 166

A 1% suspension/solution of the product of Example 157 in polyethylene glycol (Carbowax 400) was added to a dextrose nutrient broth to give a concentration of 1,000 parts per million (ppm) weight/volume of medium. Dilution in test tubes was then carried out to give a concentration of 200 ppm weight/volume of medium. To 8 ml quantities of broth was added 0.2 ml of a dense broth culture of the bacterium causing black arm of cotton, *Xanthomonas malvacearum*. After 8 days incubation at 25° C., all the broth specimens were examined for signs of bacterial growth. No growth occurred, indicating that the compound is highly bacteriostatic to this organism.

EXAMPLES 167-169

A one week old maize meal/sand culture of the damping-off disease organism *Pythium ultimum* was thoroughly mixed by hand with clean sterile John Innes No. 1 potting compost in the ratio of 3 kg culture to 12 liters of soil. The infected soil was then left for approximately 18 hours before use. Each of the compounds listed below was ground together with a wetting agent, Tween 20 (1% of final volume), until a solution or fine suspension was produced which was then diluted with distilled water to give 160 ml of solution containing 1500, 500, 150 or 50 ppm active ingredient. 15 ml aliquots of this solution were added to 75 g portions of the soil infected with *Pythium ultimum* which were contained in small plastic cartons, 60 mm diameter × 55 mm high. Fifteen cabbage seeds, variety Flower of Spring, were placed in a circular depression in the treated infected soil, recovered, and the whole sealed with a plastic cap. The cartons were then placed in a constant temperature room at 25° C. ±1° C. Four replications per treatment were made with one additional treatment where seeds were sown in soil which was chemically treated only, i.e. there was no infection. This latter treatment was included to measure the direct effect of the chemical on the germination of the seed. After six days the cartons were removed from the controlled temperature chamber and assessed for degree of fungal growth on the soil surface and percentage of seedling emergence. The results of both these assessments are expressed in a 0-8 scale as follows:

0 = <20% inhibition
1 = 20-34% inhibition
2 = 35-44% inhibition
3 = 45-54% inhibition
4 = 55-64% inhibition
5 = 65-74% inhibition
6 = 75-84% inhibition
7 = 85-94% inhibition
8 = >94% inhibition and are given in the following table:

| Example | Compound Product of Example No | Dose rate, ppm | Mycelial Control Score | Germination Score |
|---|---|---|---|---|
| 167 | 9 | 300 | 0 | 5 |
|  |  | 100 | 0 | 5 |
|  |  | 30 | 0 | 1 |
| 168 | 24 | 100 | 0 | 5 |
|  |  | 30 | 0 | 1 |
| 169 | 26 | 300 | 0 | 4 |
|  |  | 100 | 0 | 4 |
|  |  | 30 | 0 | 3 |
| Untreated | — | — | 0 | 0 |

EXAMPLES 170-178

Aqueous acetone solutions or suspensions containing 2000 or 500 mg of the compound listed below per liter, together with 125 mg of a wetting agent per liter, were applied to:

(A) the soil surrounding the roots and leaves of rice plants having two fully expanded leaves;

(B) the leaves of vine plants having five fully expanded leaves;

(C) the soil surrounding the roots of potato plants having seven fully expanded leaves;

(D) the leaves of potato plants having seven fully expanded leaves;

(E) the soil surrounding the roots and leaves of barely plants having one fully expanded leaf; or (F) the soil surrounding the roots and leaves of cucumber plants with two fully expanded leaves.

The treated plants, together with controls treated with wetting agent alone, were inoculated 24 hours after the chemical application:

in the case of (A) with an aqueous suspension of spores of the disease organism rice blast *Pyricularia oryzae*;

in the case of (B) with an aqueous suspension of sporangia of the disease organism vine downy mildew *Plasmopara viticola*;

in the case of (C) and (D) by spraying with an aqueous suspension of sporangia of the disease organism potato blight *Phytophthora infestans;* in the case of (E) by shaking with spores of the disease organism barely powdery mildew *Erysiphe graminis;* or in the case of (F) by shaking with spores of the disease organism cucumber powdery mildew *Erysiphe cichoracearum.*

The plants then:

in the case of (A) were placed in an atmosphere of 80–100% humidity at 28° C. until the disease incidence was measured seven days later;

in the case of (B) were placed in an atomosphere of 80–100% humidity at 14°–18° C. until the disease incidence was measured twelve days later;

in the case of (C) and (D) were placed in an atmosphere of 100% humidity for 24 hours and then transferred to a controlled environment room (18° C. and 80–90% relative humidity) until disease incidence was measured after 5 days;

in the case of (E) were transferred to a controlled environment room (18° C. and 80–90% relative humidity) until disease incidence was measured after 10 days; or in the case of (F) were transferred to a controlled environment room (18° C. and 80–90% relative humidity) until disease incidence was measured after fourteen days.

It was found that in comparison with less than 5% on the controls, the chemical treatments gave the percent control shown in the following table:

| Example | Compound Product of Example No | Rate, ppm | Disease | % Control |
|---|---|---|---|---|
| 170 | 141 | 2000 | rice blast | 84 |
| 171 | 29 | 2000 | vine downy mildew | 98 |
|  | " | 500 | vine downy mildew | 90 |
| 172 | 41 | 2000 | potato blight | 93 |
| 173 | 132 | 2000 | potato blight | 76 |
|  | " | 500 | potato blight | 59 |
| 174 | 148 | 2000 | barley powdery mildew | 89 |
| 175 | 147 | 2000 | barley powdery mildew | 96 |
| 176 | 146 | 2000 | barley powdery mildew | 92 |
| 177 | 123 | 2000 | barley powdery mildew | 95 |
| 178 | 123 | 2000 | cucumber powdery mildew | 92 |

EXAMPLE 179

The product of Example 95 was tested according to the procedure of Examples 49–55. It gave the following results:

| Species | Effect |
|---|---|
| Peas | 15 |
| Mustard | 100 |
| Linseed | 25 |
| Ryegrass | 15 |
| Sugarbeet | 100 |
| Oat | 20 |
| French beans | 100 |

EXAMPLES 180–184

The compounds listed below were tested according to the procedure of Example 66 but including rice (*Oryza sativa*) as an additional test species. The results were as follows:

| Example | Compound Product of Example | Wheat | Barley | Barnyard Grass | Rice |
|---|---|---|---|---|---|
| 180 | 85 | 0 | 0 | 90 | 0 |
| 181 | 131 | 5 | 10 | 90 | 0 |
| 182 | 137 | 0 | 0 | 80 | 0 |
| 183 | 150 | 0 | 0 | 80 | 0 |
| 184 | 156 | 0 | 0 | 90 | 0 |

EXAMPLE 185

The product of Example 95 was tested according to the procedure of Examples 56–60 but at 130 and 26 parts per million weight/volume. The results were as follows:

| Species | Dosage Rate, ppm | |
|---|---|---|
|  | 130 | 26 |
| Peas | 30 | 20 |
| Mustard | 100 | 90 |
| Linseed | 80 | 0 |
| Maize | 100 | 50 |
| Oats | 100 | 0 |
| Ryegrass | 100 | 90 |

EXAMPLES 186–191

Each of the compounds listed below was formulated as:

(I) an attaclay/sand dust and incorporated in John Innes I potting compost at a rate equivalent to 6.5 and 3.25 parts per million weight/volume of active ingredient to soil and placed in anodised aluminium pans, 19 cm long×9.5 cm wide×5.0 cm high. This is approximately equivalent to a surface application of 2.8 and 1.4 kg active ingredient per hectare cultivated to a depth of 5 cm. Seeds of the species listed below were sown in the treated soil, one species per pan, watered and placed in a controlled environment room (22° C.; 65–85% relative humidity and 14 hours artificial illumination at 17,000 lux) for 21 days.

(II) An aqueous suspension together with 1000 ppm of the wetting agent Lissapol NX. The surfaces of an additional set of pans with seeds already sown were then sprayed with 2.8 or 1.4 kg/ha in 450 liters/hectare, and the pans kept in the controlled environment room for 21 days.

The plants were then visually assessed for any growth regulatory or herbicidal effects. All differences from an untreated control were scored on a scale from 0–100, where 0 signifies no effect and 100 signifies complete suppression.

The results are shown in the following table where I stands for soil incorporation and II for surface spray.

| Species | Dosage Rate, ppm | 156 I | 156 II | 150 I | 150 II | 137 I | 137 II | 131 I | 131 II | 85 I | 85 II | 95 I | 95 II |
|---|---|---|---|---|---|---|---|---|---|---|---|---|---|
| Cotton | 6.5 | 0 | 0 | 0 | 0 | 0 | 0 | 0 | 0 | 0 | 0 | 5 | — |
|  | 3.25 | 0 | 0 | 0 | 0 | 0 | 0 | 0 | 0 | 0 | 0 | — | — |
| Tomato | 6.5 | 0 | 0 | 0 | 0 | 0 | 0 | 0 | 0 | 0 | 0 | 90 | — |
|  | 3.25 | 0 | 0 | 0 | 0 | 0 | 0 | 0 | 0 | 0 | 0 | — | — |
| Wheat | 6.5 | 0 | 0 | 0 | 0 | 0 | 0 | 0 | 0 | 0 | 0 | — | — |
|  | 3.25 | 0 | 0 | 0 | 0 | 0 | 0 | 0 | 0 | 0 | 0 | — | — |
| Barley | 6.5 | 0 | 0 | 0 | 0 | 0 | 0 | 0 | 0 | 0 | 0 | — | — |
|  | 3.25 | 0 | 0 | 0 | 0 | 0 | 0 | 0 | 0 | 0 | 0 | — | — |
| Barnyard Grass | 6.5 | 90 | 100 | 60 | 70 | 90 | 100 | 70 | 80 | 90 | 100 | — | — |
|  | 3.25 | 70 | 80 | 60 | 50 | 90 | 90 | 50 | 60 | 90 | 90 | — | — |
| Rice | 6.5 | 0 | 0 | 0 | 0 | 0 | 0 | 0 | 0 | 0 | 0 | — | — |
|  | 3.25 | 0 | 0 | 0 | 0 | 0 | 0 | 0 | 0 | 0 | 0 | — | — |
| Carrot | 6.5 | — | — | — | — | 0 | 0 | 0 | 0 | 0 | 0 | 0 | — |
|  | 3.25 | — | — | — | — | 0 | 0 | 0 | 0 | 0 | 0 | — | — |
| Chickweed | 6.5 | — | — | — | — | — | — | — | — | — | — | 90 | — |
| Mustard | 6.5 | — | — | — | — | — | — | — | — | — | — | 50 | — |
| Fathen | 6.5 | — | — | — | — | — | — | — | — | — | — | 100 | — |

EXAMPLE 192

2',6'-dimethyl-ethanesulphonanilide

Ethanesulphonyl chloride (114.4 g) was added slowly (during 15 minutes) to a stirred solution of 2,6-dimethylaniline (110 ml) in pyridine (500 ml). The exothermic reaction was allowed to proceed unchecked (the temperature rose to 60°), then the reaction mixture was boiled under reflux for 3 hours, cooled and poured into a rapidly stirred mixture (5 liters) of water, ice and hydrochloric acid. The precipitated, brown, granular, solid was collected by filtration, washed well with water and dried under vacuum at 50°. The yield of crude 2',6'-dimethyl-ethanesulphonanilide was 152.0 g (80%). Its melting point was 90°.

The total crude product was dissolved in 40% sodium hydroxide solution (100 ml), the solution was diluted to approximately 2 liters, warmed with charcoal for 30 minutes, then filtered. The clear, pale yellow, filtrate was cooled, then added slowly to a rapidly stirred mixture of ice, water and hydrochloric acid. The precipitated, white, solid was collected by filtration, washed with water, and dried under vacuum at 50°. The yield of purified material, melting point 92°, was 114.7 g (60%).

EXAMPLES 193–208

Following procedures analogous to that of Example 1, the following sulphonamides were prepared:

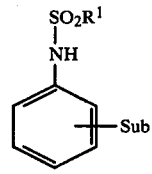

| Example | $R^1$ | Sub | Melting Point, ° |
|---|---|---|---|
| 193 | methyl | 2,3-dichloro | 102 |
| 194 | methyl | 3,4-dimethyl | 92 |
| 195 | isopropyl | 2,6-dimethyl | 102 |
| 196 | —CH$_2$COOEt | 3,4-dichloro | 104 |
| 197 | methyl | 2,6-dichloro | — |
| 198 | methyl | 2-chloro-6-methyl | 94 |
| 199 | n-butyl | 2,6-dimethyl | — |
| 200 | methyl | 2-ethyl | 40 |
| 201 | 2-thienyl | 3,4-dichloro | 138 |
| 202 | methyl | 3-chloro-4-fluoro | 116 |
| 203 | methyl | 3-chloro-4-methyl | 83 |
| 204 | methyl | 2-methanesulphonyloxy | 121–123 |
| 205 | methyl | 2,6-diisopropyl | 93 |
| 206 | methyl | 2-methanesulphonyloxy-5-nitro | 178 |
| 207 | dimethylamino | 2,6-dimethyl | — |
| 208 | dimethylamino | 2-chloro-6-methyl | — |

The NMR spectra of the compounds for whom no melting point is given in the above table have the following tau values:

| Compound of Example | Tau (CDCl$_3$) |
|---|---|
| 197 | 2.5–3.0, 3H, multiplet, (aromatic); 3.5, 1H, broad singlet, (N—H); 6.7, 3H, singlet, (CH$_3$). |
| 199 | 2.95, 3H, singlet, (aromatic); 4.2, 1H, broad singlet, (N—H); 6.8–7.0, 2H, multiplet, (S—CH$_2$); 7.65, 6H, singlet, (2,6-diCH$_3$); 7.9–8.7, 4H, multiplet, (CH$_2$CH$_2$CH$_2$CH$_3$); 9.1, 3H, triplet, (CH$_2$CH$_2$CH$_2$CH$_3$). |
| 207 | 2.95, 3H, singlet, (aromatic); 3.95, 1H, broad singlet, (N—H); 7.15, 6H, singlet, (N/CH$_3$/$_2$); 7.6, 6H, singlet, (2,6-diCH$_3$). |
| 208 | 2.75–3.0, 3H, multiplet, (aromatic); 3.8, 1H, broad singlet, (N—H); 7.2, 6H, singlet, (N/CH$_3$/$_2$); 7.55, 3H, singlet, (CH$_3$). |

EXAMPLE 209

N-2-oxopropyl-4'-chloro-methanesulphonanilide

A mixture of 4'-chloro-methanesulphonanilide (10.0 g), anhydrous potassium carbonate (4.0 g), chloroacetone (4.8 ml), and 1,2-dimethoxyethane was stirred and boiled under reflux for 24 hours, and then filtered, and the filtrate was evaporated. The oil residue was dissolved in ether, and the solution was washed with water, dried (MgSO$_4$) and evaporated. The residue gave almost colourless crystals from acetone/40°–60° petrol. Melting point 108°. Yield 4.1 g.

EXAMPLES 210–221

In a similar way to Example 209, the following were prepared:

N-2-oxopropyl-2'-chloro-6'-methyl-methanesulphonanilide, melting point 96°;
N-2-oxopropyl-2',6'-dimethyl-methanesulphonanilide, melting point 56°;
N-2-oxo-3,3-dimethylbutyl-2',6'-dimethyl-ethanesulphonanilide,
analysis: Found: C 61.75, H 8.26, N 4.62. C$_{16}$H$_{25}$NO$_3$S requires: C 61.70, H 8.09, N 4.50.
N-2-oxopropyl-2',6'-dimethyl-ethanesulphonanilide, melting point 68°;
N-2-oxopropyl-2',6'-dimethyl-1-propanesulphonanilide, melting point 104°;
N-2-oxopropyl-2',6'-dimethyl-2-thiophenesulphonanilide, melting point 127°–128°;
N-2-oxopropyl-2',6'-diethyl-methanesulphonanilide, melting point 46°;
N-2-oxopropyl-2',6'-dimethyl-1-butanesulphonanilide, melting point 69°;
N-2-oxopropyl-3',4'-dichloro-methanesulphonanilide, melting point 92°;
N-2-oxopropyl-3',4'-diisopropyl-methanesulphonanilide, melting point 134°;
N-2-oxopropyl-2'-methoxy-methanesulphonanilide, melting point 126°; and
N-2-oxopropyl-2',5'-dichloro-methanesulphonanilide, melting point 134°.

EXAMPLE 222

N-(2,2-dimethoxypropyl)-2'-chloro-6'-methyl-methanesulphonanilide

To a solution of N-(2-oxopropyl)-2'-chloro-6'-methyl-methanesulphonanilide (5.7 g) in methanol (80 ml) was added 4-toluenesulphonic acid (0.2 g), followed by trimethyl orthoformate (6.65 ml). The mixture was stirred at room temperature for 24 hours, then allowed to stand for 6 days. The solution was poured into dilute sodium bicarbonate solution, and the precipitated solid was collected by filtration, washed with water, and dried to give an off-white coloured solid of melting point 84°. Yield 6.0 g.

EXAMPLES 223 AND 224

In a similar way to Example 222, the following were prepared:
N-(2,2-dimethoxypropyl)-4'-chloro-methanesulphonanilide, melting point 85°; and
N-(2,2-dimethoxypropyl)-2',6'-dimethyl-methanesulphonanilide, melting point 82°.

EXAMPLE 225

4'-chloro-N-[(2-methyl-1,3-dithiolan-2-yl)methyl]-methanesulphonanilide

A solution of 4'-chloro-N-(2,2-dimethoxypropyl)-methanesulphonanilide (3.2 g) in acetic acid (50 ml) was treated with ethanedithiol (0.96 ml) and the mixture was slowly distilled, using a short Vigreux column, for 30 minutes, and the distillate discarded. The remaining acetic acid solution was evaporated, and the residue was re-evaporated with toluene to remove traces of acetic acid. A solution of the residue in ether deposited pink coloured crystals on standing. Recrystallisation from ethyl acetate/ether gave the product as nearly white crystals of melting point 114°–117°.

EXAMPLES 226 AND 227

In a similar way to Example 225, the following were prepared:
N-[(2-methyl-1,3-dithiolan-2-yl)methyl]-2',6'-dimethyl-methanesulphonanilide, melting point 108°; and
N-[(2-methyl-1,3-dithiolan-2-yl)methyl]-2'-chloro-6'-methylmethanesulphonanilide, melting point 140°.

EXAMPLE 228

N-[(2-methyl-1,3-dioxolan-2-yl)methyl]-4'-chloro-methanesulphonanilide

A mixture of N-(2-oxopropyl)-4'-chloromethanesulphonanilide (6.0 g), ethane-1,2-diol (10 ml), 4-toluenesulphonic acid (0.1 g) and toluene (75 ml) was stirred and boiled under reflux with water separation by means of a Dean and Stark receiver. After 3 hours the reaction mixture was cooled and poured into water (about 200 ml) containing a few drops of sodium hydroxide solution. The organic layer was separated, washed with water, dried (MgSO$_4$) and evaporated to a brown oil, which gave fawn coloured crystals from a solution in toluene/80°–100° petrol. Yield 6.0 g (86%). Melting point 84°–85°.

EXAMPLES 229–231

In a similar way to Example 228, the following were prepared:
N-[(2-methyl-4-hydroxymethyl-1,3-dioxolan-2-yl)methyl]-4'-chloro-methanesulphonanilide, melting point 118°;
N-[(2-methyl-1,3-dioxolan-2-yl)methyl]-2'-chloro-6'-methylmethanesulphonanilide, melting point 84°; and
N-[(2-methyl-1,3-dioxolan-2-yl)methyl]-2',6'-dimethyl-methanesulphonanilide, melting point 58°.

EXAMPLE 232

N-2-hydroxyiminopropyl-2',6'-dimethyl-methanesulphonanilide

A solution of N-(2-oxopropyl)-2',6'-dimethyl-methanesulphonanilide (3.0 g) in ethanol (50 ml) was added to a solution of hydroxylamine hydrochloride (0.9 g) and sodium acetate (1.1 g) dissolved in the minimum volume of water. The solution was boiled under reflux for 3 hours, and then cooled and evaporated. A solution of the residue in ether was washed with water, dried (MgSO$_4$) and evaporated. The residue was re-evaporated with toluene to remove acetic acid, then the product was crystallised from an ethyl acetate solution. Melting point 122°–124°.

EXAMPLES 233 & 234

One week old maize meal/sand culture of the damping-off disease organism *Pythium ultimum* was thoroughly mixed by hand with clean sterile John Innes No. 1 potting compost in the ratio of 3 kg culture to 12 liters of soil. This infected soil was then left for approximately 18 hours before use. The compounds listed in the Table below were each ground with the wetting agent Tween 20 (1% of final volume), until a solution or fine suspension was produced, which was then diluted with distilled water to give 160 ml of solution containing 1500 or 500 parts per million (ppm) active ingredient. 15 ml aliquots of this solution were added to 75 g portions of the soil infected with *Pythium ultimum* which were contained in small plastic cartons, 60 mm diameter×55 mm high.

Fifteen cabbage seeds, variety Flower of Spring, were placed in a circular depression in the treated infected soil, recovered, and the whole sealed with a plastic cap. The cartons were then placed in a constant temperature room at 25° C.±1° C. Four replications per treatment were made, with one additional treatment where seeds were sown in soil which was chemically treated only, i.e. there was no infection. This latter treatment was included to measure the direct effect of the chemical on the germination of the seed.

After six days, the cartons were removed from the controlled temperature chamber and assessed for degree of fungal growth on the soil surface and percentage of seedling emergence. The results of both these assessments are expressed in a 0–8 scale as follows:

| | |
|---|---|
| 0 = <20% inhibition | 5 = 65–74% inhibition |
| 1 = 20–34% inhibition | 6 = 75–84% inhibition |
| 2 = 35–44% inhibition | 7 = 85–94% inhibition |
| 3 = 45–54% inhibition | 8 = >94% inhibition |
| 4 = 55–64% inhibition | | and are given in the following table. Any phytotoxicity induced by the chemical alone is deduced from the chemical only soil treatment.

| Compound | Dose, ppm | Mycelial Control Score | Germination Score | Phytotoxicity Score |
|---|---|---|---|---|
| N-[(2-methyl-1,3-dioxolan-2yl)methyl]-4'-chloro-methane-sulphonanilide | 300 | 8 | 0 | — |
| N-(2,2-dimethoxy-propyl)-2'-chloro-6'-methyl-methane-sulphonanilide | 300 | 4 | 1 | 0 |
| | 100 | 3 | 1 | 0 |
| Untreated | 0 | 0 | 0 | |

EXAMPLE 235 & 236

Aqueous acetone solutions of each of the compounds listed in the Table below, containing 2000 parts per million (ppm), together with 125 ppm of a suitable wetting agent, were applied to the soil surrounding the roots and leaves of vine plants having five fully expanded leaves.

The treated plants, together with controls treated with wetting agent alone, were inoculated 24 hours after the chemical application with an aqueous suspension of sporangia of the disease organism known as vine downy mildew, *Plasmopara viticola*.

The plants were then placed in an atmosphere of 100% humidity/80% humidity, at 14°–18° C. until the disease incidence was measured twelve days later, when it was found that the treatments had given the following fungal control in comparison with less than 5% on the controls.

| Compound | % Control Vine Downing Mildew |
|---|---|
| N-(2,2-dimethoxypropyl)-2'chloro-6'-methyl-methanesulphonanilide | 94 |
| N-[(2-methyl-1,3-dioxolan-2-yl)methyl]-2'-chloro-6'-methyl-methanesulphonanilide | 80 |

EXAMPLES 237–239

Aqueous acetone solutions of each of the compounds listed below, containing 2,000, 500 or 125 per million (ppm) weight/volume together with 125 ppm of a suitable wetting agent, were applied to the soil surrounding the roots and leaves of potato plants having seven fully expanded leaves.

The treated plants, together with controls treated with wetting age alone, were inoculated 24 hours after the chemical application with an aqueous suspension of sporangia of the disease organism known as potato blight, *Phytophthora infestans*.

The plants were then placed in an atmosphere of 100% humidity/80% humidity for 24 hours, and then transferred to a controlled environment room (18° C. and 80–90% relative humidity) until disease incidence was measured after five days.

It was found that the treatments had given the degree of fungal control shown in the following Table, compared with less than 5% on the controls.

| Compound | Dose, ppm | % Control Potato Blight |
|---|---|---|
| N-2-oxopropyl-2',6'-dimethyl-methane-sulphonanilide | 2,000 | 99 |
| | 500 | 94 |
| | 125 | 90 |
| N-(2,2-dimethoxypropyl)-2',6'-dimethyl-methanesulphonanilide | 2,000 | 98 |
| | 500 | 55 |
| N-[(2-methyl-1,3-dioxolan-2-yl)methyl]-2'-6'-dimethyl-methanesulphonanilide | 2,000 | 98 |

EXAMPLE 240

Aqueous acetone solutions of N-2-oxo-3,3-dimethyl-butyl-2',6'-dimethyl-ethanesulphonanilide, containing 2,000 parts per million (ppm) weight/volume together with 125 ppm of a suitable wetting agent were applied to the soil surrounding the roots and leaves of rice plants having two fully expanded leaves.

The treated plants, together with controls treated with wetting agent alone, were inoculated 24 hours after the chemical application with an aqueous suspension of spores of the disease organism known as rice blast, *Pyricularia oryzae*.

The plants were then placed in an atomsphere of 100% humidity/80% humidity, at 28° C., until the disease incidence was measured seven days later, when it was found that the treatment had given 80% fungal control in comparison with less than 5% on the controls.

EXAMPLE 241

N-(2-oxopropyl)-2'-chloro-6'-methyl-methanesulphonanilide, formulated as an attaclay/sand dust, was incorporated in John Innes I potting compost at a rate equivalent to 130 parts per million weight/volume of active ingredient to soil and placed in anodised aluminium pans, 19 cm long×9.5 cm wide×5.0 cm deep. These rates are approximately equivalent to a soil surface application of 56 kg active ingredient per hectare cultivated to a depth of 5 cm. Seeds of Peas, Mustard, Linseed, Maize, Oats and Ryegrass were sown in the treated soil, watered and placed in a controlled environment room (22° C.; 65–85% relative humidity; 14 hours artificial illumination at 13000 lux) for 21 days.

The plants were then visually assessed for any growth regulatory or herbicidal effects. All differences from an untreated control were scored on a scale from 0–100, where 0 signifies no effect and 100 signifies complete suppression.

The results are shown in the following table:

| Species | Dosage rate (ppm) | 130 |
| --- | --- | --- |
| Peas | (Pisum sativum) | 30 |
| Mustard | (Sinapis alba) | 100 |
| Linseed | (Linum usitatissimum) | 80 |
| Maize | (Zea mays) | 5 |
| Oats | (Avena sativa) | 60 |
| Ryegrass | (Lolium perenne) | 70 |

EXAMPLE 242

A 30% solution of sulphuric acid (27.5 ml) is added dropwise to a stirred mixture of N-(2-oxopropyl)-2',6'-dimethyl-methanesulphonanilide (0.1 mole), potassium cyanide (6.2 g) and water (20 ml). The temperature is kept at 15°. The reaction mixture is stirred for 15 minutes and the cyanohydrin of the sulphonanilide is isolated.

EXAMPLE 243

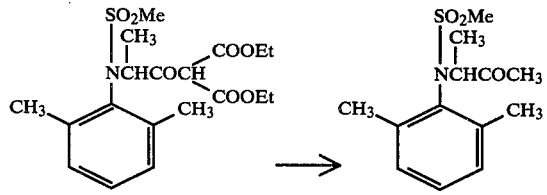

A mixture of N-[3,3-di(ethoxycarbonyl)-2-oxo-1-methylpropyl]-2',6'-dimethyl-methane sulphonanilide (0.5 mole), sodium hyroxide (1.5 mole), ethanol (500 ml) and water (500 ml) is heated for 2½ hours, cooled and the ethanol evaporated. The resulting aqueous solution is acidified with hydrochloric acid and heated for 1 hour, and then the product is isolated.

EXAMPLE 244

A mixture of 2,6-dimethylmethanesulphonanilide (12.5 g), 2'-chloro-4-thiocyanoacetanilide (14.2 g), potassium carbonate (4.3 g) and dimethylformamide (75 ml) was stirred and heated to 70°–80° for 3 hours, then poured into ice/water. The precipitated viscous semi-solid material was extracted into chloroform. The chloroform solution was washed with 5% sodium hydroxide solution, washed with water, then dried (MgSO₄) and evaporated to a brown oil. A solution of this oil in chloroform was percolated through a short column of silica gel. Evaporation of the eluate gave a brown oil which deposited almost colourless crystals of N-[[(4-thiocyanophenyl)carbamoyl]methyl]2',6'-dimethylmethanesulphonanilide from a solution in ethylacetate. Melting point 152°.

EXAMPLE 245

A solution of N-(3-hydroxy-2-oxopropyl)-2',6'-dimethylmethanesulphonanilide (2.8 g) in pyridine (5 ml) and acetic anhydride (5 ml) was allowed to stand at room temperature for 20 hours. Water was added to decompose excess anhydride, and the oily product was extracted into ether. The ether solution was washed successively with dilute hydrochloric acid and sodium bicarbonate solution, dried (MgSO₄), and evaporated to give a yellow oil. A solution of this oil in chloroform was percolated through a short column of silica gel. Evaporation of the eluate gave the product, N-(3-acetoxy-2-oxopropyl)-2',6'-dimethylmethanesulphonanilide, as a pale yellow oil.

Yield 2.5 g (77%).

Analysis: C, 53.20; H, 6.57; N, 4.30%. $C_{14}H_{19}NO_5S$ requires C, 53.66; H, 6.11; N, 4.47%.

EXAMPLE 246

A solution of N-[1-(2-(ethoxycarbonyl)hydrazinocarbonyl)ethyl]-2',6'-dimethylmethanesulphonanilide (5.6 g) in ethanol (75 ml) and 10% sodium hydroxide solution (75 ml) was heated on a steam bath for 2½ hours, and then the ethanol was evaporated off. The aqueous solution remaining was acidified with dilute hydrochloric acid, heated on a steam bath for 1 hour, and then filtered. The filtrate was just neutralised with dilute sodium hydroxide solution, saturated with sodium chloride and extracted with chloroform. The chloroform solution was dried and evaporated, and the residue gave colourless crystals of N-[1-(hydrazinocarbonyl)ethyl]-2',6'-dimethylmethanesulphonanilide from a solution in toluene/60°–80° petrol. Yield 2.6 g (58%). Melting point 115°–118°.

EXAMPLE 247

A solution of the hydrochloride salt of N-[1-(hydrazinocarbonyl)-ethyl]-2',6'-dimethylmethanesulphonanilide (3.2 g) and acetylacetone (1.0 ml) in ethanol (25 ml) was heated to boiling, and then allowed to cool to room temperature during 2 hours. The precipitated solid was collected by filtration and recrystallised from ethanol to give N-[3-(3,5-dimethyl-1-pyrazolyl)-1-methyl-2-oxo-ethyl]-2',6'-dimethylmethanesulphonanilide. Yield 1.5 g (43%). Melting point 168°.

EXAMPLE 248

Methyl isocyanate (1.2 ml) was added to an acetone solution of N-[2-hydroxyiminopropyl]-2',6'-dimethylmethanesulphonanilide (2.7 g) containing triethylamine (0.05 ml). The mixture was allowed to stand at room temperature overnight, then evaporated to a viscous oil which slowly solidified on standing. Recrystallisation from ethylacetate/60°–80° petrol gave colourless crystals of N-[2-(methylcarbamoyloxyimino)propyl]-2',6'-dimethylmethanesulphonanilide. Yield 3.0 g (91%). Melting point 130°–134°.

EXAMPLE 249

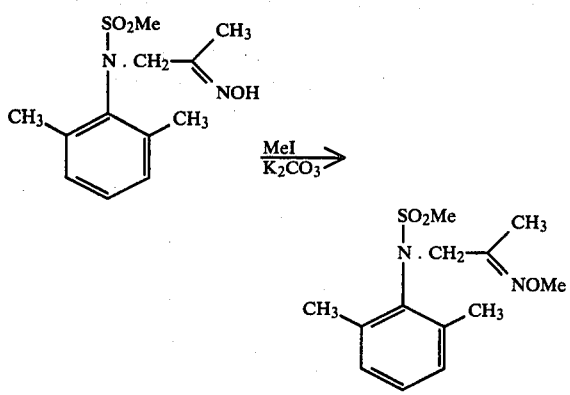

A mixture of N-[2-hydroxyiminopropyl]-2',6'-dimethylmethanesulphonanilide (2.7 g), potassium carbonate (0.75 g), iodomethane (1.3 ml) and acetone (50 ml) was stirred and boiled gently under reflux for 3 hours. The reaction mixture was filtered, and the filtrate evaporated to an oil, which deposited crystals from a solution in ether/40°–60° petrol. Yield 0.6 g (21%). Melting point 126°.

EXAMPLE 250

Acetyl chloride (0.9 ml) was added to a dichloromethane (20 ml) solution of N-[2-hydroxyiminopropyl]-2',6'-dimethylmethanesulphonanilide (2.6 g) and triethylamine (1.6 ml). The mixture was stirred and boiled under reflux for 3 hours, then filtered, and the filtrate evaporated to a clear yellow oil. A solution of this oil in chloroform was percolated through a short column of silica gel, and the eluate evaporated to give analytically pure N-[2-(acetyloxyimino)propyl]-2',6'-dimethylmethanesulphonanilide. Yield 1.9 g (63%).

Analysis: Found: C, 53.74; H, 6.80; N, 8.49%. $C_{14}H_{20}N_2O_4S$ requires: C, 53.83; H, 6.45; N, 8.97%.

EXAMPLE 251

A solution of diethyl ethoxymagnesium malonate was prepared by refluxing a mixture of magnesium (0.9 g), diethyl malonate (5.6 ml), ethanol (4.3 ml) and ether (20 ml) for 3 hours, then evaporating with toluene and replacing the solvent with dry ether. To this solution was added dropwise with stirring an ethereal solution of N-(1-chlorocarbonylethyl)-2',6'-dimethyl-methane sulphonanilide (prepared from the acid (10 g) and thionyl chloride). After stirring overnight at room temperature, the resulting complex was decomposed by warming with dilute sulphuric acid. Organic products were extracted into ether and the solution was washed with water, dried (MgSO₄), and evaporated to give a solid residue. Recrystallisation from ethyl acetate gave colourless crystals of N-[3,3-di(ethoxycarbonyl)-2-oxo-1-methylpropyl]-2',6'-dimethyl-methanesulphonanilide. Melting point 125°.

EXAMPLE 252

A solution of N-[1-ethoxycarbonylethyl]-2'-trifluoromethyl-4'-phenylthio-methanesulphonanilide (7.5 g) in acetic acid (50 ml) was heated to boiling with stirring, and hydrogen peroxide (6 ml of 100 vols) was added. Stirring and boiling under reflux were continued for 3 hours, then the reation mixture was poured into ice/water and extracted with chloroform. The chloroform solution was dried and evaporated to a yellow oil which gave colourless crystals of N-[1-ethoxycarbonylethyl]-2'-trifluoromethyl-4'-phenylsulphonyl-methane-sulphonanilide from an ethanol solution. Yield 6.6 g (83%). Melting point 121°.

EXAMPLE 253

A solution of N-carboxymethyl-2',6'-dimethyl-methanesulphonanilide (7.2 g) in chloroform (50 ml) was treated with thionyl chloride (5 ml), and the mixture was boiled under reflux for 1½ hours, then evaporated. The residue was re-evaporated with toluene (to remove traces of thionyl chloride), and then dissolved in dry tetrahydrofuran (10 ml). Tris-trimethylsilyloxyethylene (19.6 g) was added followed by stannic chloride (3 drops). The reaction mixture was allowed to stand at room temperature for 70 hours, then was heated on a steam bath for 2 hours, and poured into a mixture of equal volumes of dilute hydrochloric acid and tetrahydrofuran. This solution was heated on the steam bath for ½ hour, saturated with salt, and extracted with ether. The combined ether solution was washed with sodium bicarbonate solution, dried (MgSO₄) and evaporated to give the product, N-[3-hydroxy-2-oxo-propyl]-2',6'-dimethyl-methanesulphonanilide, as a clear yellow oil. Yield 5.0 g (66%).

Analysis: C, 57.72; H, 6.40; N, 4.91%. $C_{12}H_{17}NO_4S$ requires: C, 53.12; H, 6.32; N, 5.16%.

EXAMPLE 254

Following a procedure analogous to that of Example 253, N-[3-hydroxy-2-oxo-1-methylpropyl]-2',6'-dimethyl-methanesulphonanilide was prepared. Melting point 125°–126°.

EXAMPLES 255 AND 256

In a similar way to Examples 193–208, 2',6'-dimethyl-4-morpholinesulphonanilide, melting point 124°, and 3',4'-dichloro-4-morpholinesulphonanilide, melting point 122°, were prepared.

EXAMPLES 257–259

In a similar way to Example 3, the following esters of formula given in Examples 4–33 were prepared:

| Example | R¹ | R¹⁸ | A | Sub | Melting Point |
|---|---|---|---|---|---|
| 257 | n-Pr | Me | COOCH₂—⟨furan⟩ | 2,6-diMe | Oil |
| 257a | Me | H | CH=CHCOOEt | 2-Cl,6-Me | 70° |
| 258 | Me | Me | COOEt | 3,5-diCl | 92° |
| 259 | Me | Me | COOMe | 3,5-diCl | 100° |

The analysis for the compound of Example 257 is as follows: Found: 60.63% C, 7.00% H, 3.69% N; $C_{19}H_{25}NO_5S$ requires: 60.14% C, 6.64% H, 3.69% N.

EXAMPLES 260 AND 261

In a similar way to Example 34, the following compounds of formula given in Examples 35–43 were prepared.

| Example | R¹ | R¹⁸ | A | Sub | Melting Point |
|---|---|---|---|---|---|
| 260 | Me | H | CON⟨O⟩ | 2,6-diMe | 109° |
| 261 | Me | Me | CON⟨O⟩ | 3,5-diCl | 210° |

EXAMPLE 262

In a similar way to Example 209, N-(2-oxopropyl)-3',5'-dichloromethanesulphonanilide, melting point 106°, was prepared.

EXAMPLE 263

In a similar way to Example 44, N-(3-cyanopropyl)-3',5'-dichloro-methanesulphonanilide, melting point 82°, was prepared.

EXAMPLE 264

In a similar way to Example 123, the lactone

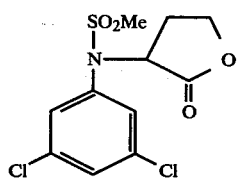

melting point 128°, was prepared.

EXAMPLE 265

In a similar way to Example 85, N-(thiocarbamoylmethyl)-3',5'-dichloro-methanesulphonanilide, melting point 188°, was prepared.

EXAMPLE 266

A 40% weight/volume emulsifiable concentrate was prepared by making a xylene solution of the following:

| | |
|---|---|
| N-(1-(ethoxycarbonyl)ethyl)-2',6'-dimethyl-1-propanesulphonanilide | 400g |
| Arylan CA (calcium dodecylbenzenesulphonate 70% in butanol) | 25g |
| Ethylan C40AH (castor oil/ethylene oxide condensate) | 25g |
| Xylene (to 1 liter) | approx 600 ml |

EXAMPLE 267

A 25% weight/volume emulsifiable concentrate was prepared by making a xylene solution of the following:

| | |
|---|---|
| N-(1-(ethoxycarbonyl)ethyl)-2',6'-dimethyl-ethanesulphonanilide | 250g |
| Arylan CA | 25g |
| Ethylan C40AH | 25g |
| Xylene (to 1 liter) | approx 740 ml |

EXAMPLE 268

N-(2-oxopropyl)-3',4'-dimethyl-methanesulphonanilide was tested at a dose rate of 300 ppm in the test described in Examples 233 and 234. It gave a mycelial control score of 0 and a germination score of 3 whereas the untreated samples gave a score of 0 for both.

EXAMPLES 269–271

The compounds listed below were tested in the test described in Examples 170–178, with the following results:

| Example | Compound | Rate, ppm | Disease | % Control |
|---|---|---|---|---|
| 269 | Product of Example 46 | 2000 | potato blight | 56 |
| 270 | N-(2-oxopropyl)-3',4'-dimethyl-methane sulphonanilide | 2000 | rice blast | 67 |
| | N-(2-oxopropyl)-3',4'-dimethyl-methane sulphonanilide | 2000 | barley powdery mildew | 99 |
| | N-(2-oxopropyl)-3',4'-dimethyl-methane sulphonanilide | 2000 | potato blight | 62 |
| 271 | Product of Example 249 | 500 | potato blight | 74 |
| | Product of Example 249 | 500 | rice blast | 66 |

EXAMPLE 272

In a similar way to Example 209, N-(2-oxopropyl)-3',4'-dimethylmethanesulphonanilide, melting point 78°, was prepared.

I claim:

1. A compound which is a sulphonanilide of the formula

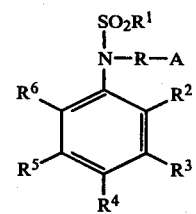

or salt thereof, wherein $R^1$ represents alkyl of 1–15 carbon atoms; alkyl of 1–15 carbon atoms substituted by one or more of halogen, and alkoxy of 1–6 carbon atoms;

R represents alkylene or alkenylene of up to 6 carbon atoms;

A represents —CEGR⁹ where E and G are the same and each represents an oxygen atom; $R^9$ represents alkyl of 1–15 carbon atoms; alkyl of 1–15 carbon atoms substituted by one or more of halogen, alkoxy of 1–6 carbon atoms, hydroxy, amino and amino mono or di-substituted by groups selected from alkyl of 1–15 carbon atoms and alkanoyl of 2–7 carbon atoms; phenylalkyl of 7–10 carbon atoms; phenylalkyl of 7–10 carbon atoms substituted on the phenyl nucleus by one or more of halogen, alkyl of 1–6 carbon atoms, alkoxy of 1–6 carbon atoms, nitro, and trifluoromethyl; cycloalkyl of 3–7 carbon atoms; phenyl; or phenyl substituted by one or more of halogen, alkyl of 1–6 carbon atoms, alkoxy of 1–6 carbon atoms, nitro, and trifluoromethyl; and $R^2$, $R^3$, $R^4$, $R^5$ and $R^6$ are the same or different and each represents a hydrogen atom; alkyl of 1–15 carbon atoms; alkyl of 1–15 carbon atoms substituted by one or more of halogen, alkoxy of 1–6 carbon atoms, hydroxy, amino and amino mono- or di-substituted by groups selected from alkyl of 1–15 carbon atoms and alkanoyl of 2–7 carbon atoms; hydroxy; alkoxy of 1–6 carbon atoms; nitro; a halogen atom; amino; amino or mono- or di-substituted by groups selected from alkyl of 1–15 carbon atoms and alkanoyl of 2–7 carbon atoms.

2. A compound defined in claim 1 which is a sulphonanilide of the formula

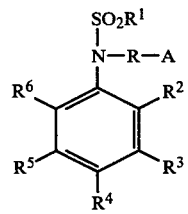

or salt thereof, wherein $R^1$ represents alkyl of 1–4 carbon atoms;

R represents alkylene of 1–3 carbon atoms or alkenylene of 3 carbon atoms;

A represents —COOR$^{17}$ where $R^{17}$ represents alkyl of 1–8 carbon atoms;

3 or 4 of $R^2$, $R^3$, $R^4$, $R^5$ and $R^6$ each represent a hydrogen atom and the remainder are the same or different and each represents alkyl of 1–3 carbon atoms, halogen, hydroxy, nitro, alkoxy of 1–6 carbon atoms, trifluoromethyl.

3. A compound defined in claim 1 which is a sulphonanilide of the formula

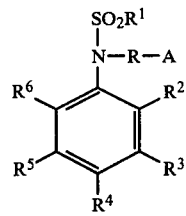

or salt thereof, wherein
$R^1$ represents alkyl of 1–15 carbon atoms; alkyl of 1–15 carbon atoms substituted by one or more of halogen, and alkoxy of 1–6 carbon atoms;
R represents alkylene of 1–6 carbon atoms;
A represents —CEGR$^9$ where E and G are the same and each represents an oxygen atom; $R^9$ represents alkyl of 1–15 carbon atoms; alkyl of 1–15 carbon atoms substituted by one or more of halogen, alkoxy of 1–6 carbon atoms, amino and amino mono- or di-substituted by groups selected from alkyl of 1–15 carbon atoms and alkanoyl of 2–7 carbon atoms; phenylalkyl of 7–10 carbon atoms; phenylalkyl of 7–10 carbon atoms substituted on the phenyl nucleus by one or more of halogen, alkyl of 1–6 carbon atoms, alkoxy of 1–6 carbon atoms, nitro and trifluoromethyl; phenyl; or phenyl substituted by one or more of halogen, alkyl of 1–6 carbon atoms; alkoxy of 1–6 carbon atoms, nitro and trifluoromethyl; and
$R^2$, $R^3$, $R^4$, $R^5$ and $R^6$ are the same or different and each represents a hydrogen atom; alkyl of 1–15 carbon atoms; alkyl of 1–15 carbon atoms substituted by one or more of halogen, alkoxy of 1–6 carbon atoms, amino and amino mono- or di-substituted by groups selected from alkyl of 1–15 carbon atoms and alkanoyl of 2–7 carbon atoms; alkoxy of 1–6 carbon atoms; nitro; amino or a halogen atom.

4. A compound as defined in claim 1 wherein 3 or 4 of $R^2$, $R^3$, $R^4$, $R^5$ and $R^6$ each represent a hydrogen atom.

5. A compound as defined in claim 1 selected from the group N-(1-[ethoxycarbonyl]ethyl)-2',6'-dimethyl-1-propane-sulphonanilide; N-(1-[ethoxycarbonyl]ethyl)-2',6'-dimethylethanesulphonanilide; or N-(1-(methoxycarbonyl)ethyl)-2',6'-dimethyl-methanesulphonanilide.

6. The compound of claim 5 which is N-(1-[ethoxycarbonyl]ethyl 2',6'-dimethyl-1-propanesulphonanilide.

7. The compound of claim 5 which is N-(1-[ethoxycarbonyl]ethyl)-2',6'-dimethylethanesulphonanilide.

8. The compound of claim 5 which is N-(1-[methoxycarbonyl]ethyl)-2',6'-dimethyl-methanesulphonanilide.

* * * * *